United States Patent
Chevalier et al.

(10) Patent No.: US 9,102,919 B2
(45) Date of Patent: Aug. 11, 2015

(54) WNT PATHWAY STIMULATION IN REPROGRAMMING SOMATIC CELLS WITH NUCLEAR REPROGRAMMING FACTORS

(75) Inventors: Brett Chevalier, Malden, MA (US); Alexander Marson, Cambridge, MA (US); Richard A. Young, Weston, MA (US); Ruth Foreman, Somerville, MA (US); Rudolf Jaenisch, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 790 days.

(21) Appl. No.: 12/675,681

(22) PCT Filed: Aug. 29, 2008

(86) PCT No.: PCT/US2008/010249
§ 371 (c)(1),
(2), (4) Date: Aug. 24, 2010

(87) PCT Pub. No.: WO2009/032194
PCT Pub. Date: Mar. 12, 2009

(65) Prior Publication Data
US 2010/0310525 A1  Dec. 9, 2010

Related U.S. Application Data

(60) Provisional application No. 60/967,028, filed on Aug. 31, 2007, provisional application No. 61/188,190, filed on Aug. 6, 2008.

(51) Int. Cl.
*C12N 15/02* (2006.01)
*C12N 5/074* (2010.01)

(52) U.S. Cl.
CPC ........ *C12N 5/0696* (2013.01); *C12N 2501/415* (2013.01); *C12N 2501/602* (2013.01); *C12N 2501/603* (2013.01); *C12N 2501/604* (2013.01); *C12N 2502/45* (2013.01); *C12N 2502/99* (2013.01); *C12N 2510/00* (2013.01)

(58) Field of Classification Search
CPC .................. C12N 2501/602; C12N 2501/603; C12N 5/0696; C12N 2510/00; C12N 2501/604; C12N 15/85; C12N 2501/605; C12N 2501/608; C12N 2501/606; C12N 2502/45; C12N 2502/99; C12N 2506/45; C12N 5/16
See application file for complete search history.

(56) References Cited

U.S. PATENT DOCUMENTS

| 6,057,117 A | 5/2000 | Harrison et al. |
| 6,608,063 B2 | 8/2003 | Nuss et al. |
| 7,682,828 B2 | 3/2010 | Jaenisch et al. |
| 8,071,369 B2 | 12/2011 | Jaenisch et al. |
| 2003/0181439 A1 | 9/2003 | Meijer et al. |
| 2004/0087016 A1 | 5/2004 | Keating et al. |
| 2004/0092535 A1 | 5/2004 | Barasanti et al. |
| 2004/0209878 A1 | 10/2004 | Guzi et al. |
| 2005/0054663 A1 | 3/2005 | Bennett et al. |
| 2006/0030042 A1* | 2/2006 | Brivanlou et al. ............ 435/366 |
| 2008/0014638 A1 | 1/2008 | Smith et al. |
| 2008/0066197 A1 | 3/2008 | Ying et al. |
| 2009/0047263 A1* | 2/2009 | Yamanaka et al. ......... 424/93.21 |
| 2010/0041137 A1 | 2/2010 | Smith et al. |
| 2010/0144031 A1 | 6/2010 | Jaenisch et al. |
| 2011/0076678 A1 | 3/2011 | Jaenisch et al. |
| 2011/0088107 A1 | 4/2011 | Hanna et al. |
| 2012/0028821 A1 | 2/2012 | Jaenisch et al. |
| 2012/0034192 A1 | 2/2012 | Young et al. |

FOREIGN PATENT DOCUMENTS

| EP | 1970446 | 9/2008 |
| WO | WO 02-085909 | 10/2002 |
| WO | WO 03-011287 | 2/2003 |
| WO | WO 03-049739 | 6/2003 |
| WO | WO 2005-039485 | 5/2005 |
| WO | WO 2006-091737 | 8/2006 |
| WO | WO 2007-069666 | 6/2007 |
| WO | WO 2008-015418 | 2/2008 |
| WO | WO-2009-032194 | 3/2009 |

(Continued)

OTHER PUBLICATIONS

Wiese et al. Signals from Embryonic Fibroblasts Induce Adult Intestinal Epithelial Cells to Form Nestin-Positive Cells with Proliferation and Multilineage Differentiation Capacity in Vitro. Stem Cells, vol. 24, pp. 2085-2097, published online Jun. 1, 2006.*

Cho et al. Endogenous Wnt Signaling Promotes Proliferation and Suppresses Osteogenic Differentiation in Human Adipose Derived Stromal CellsTissue Engineering, Jan. 2006, pp. 111-121.*

SStadtfeld et al. "Induced Pluripotent Stem Cells Generated Without Viral Integration." Science, 322, 945-949, 2008tadtfeld (Science 7 2008: vol. 322 No. 5903 p. 945-949).*

Gonzalez et al "Generation of mouse-induced pluripotent stem cells by transient expression of a single nonviral polycistronic vector." PNAS, 106:22, 8918-8922, 2009.*

Okita et al. "Generation of Mouse Induced Pluripotent Stem Cells Without Viral Vectors." Science, 322, 949-953, 2008.*

Yamanaka et al. Induction of pluripotent stem cells from mouse fibroblasts by four transcription factors. Cell Prolif. 41, 51-56. 2008.*

(Continued)

*Primary Examiner* — Deborah Crouch
(74) *Attorney, Agent, or Firm* — Lisa M. Warren, Esq.; Morse, Barnes-Brown & Pendleton, P.C.

(57) ABSTRACT

The invention provides compositions and methods of use in reprogramming somatic cells. Compositions and methods of the invention are of use, e.g., for generating or modulating (e.g., enhancing) generation of induced pluripotent stem cells by reprogramming somatic cells. The reprogrammed somatic cells are useful for a number of purposes, including treating or preventing a medical condition in an individual. The invention further provides methods for identifying an agent that reprograms somatic cells to a pluripotent state and/or enhances the speed and/or efficiency of reprogramming. Certain of the compositions and methods relate to modulating the Wnt pathway.

12 Claims, 5 Drawing Sheets

(56) References Cited

FOREIGN PATENT DOCUMENTS

| WO | WO 2009-101407 | 8/2009 |
|---|---|---|
| WO | WO 2010-124290 | 10/2010 |

OTHER PUBLICATIONS

Niwa et al. "Quantitative expression of Oct-3/4 defines differentiation, dedifferentiation or self-renewal of ES cells." Nature Genetics, 24, 372-376, 2000.*
Lewitzky et al. "Reprogramming somatic cells towards pluripotency by defined factors." Current Opinion in Biotechnology 18,467-473, 2007.*
Hwang et al. "Wnt-3a regulates chondrocyte differentiation via c-JUN/AP-1 pathway," FEBS Letters, 579: 4837-4842 (2005).
Marson et al., "Wnt signaling promotes reprogramming of somatic cells to pluripotency," Cell Stem Cell, 3(2):132-135 (2008).
Meissner et al., "Direct reprogramming of genetically unmodified fibroblasts into pluripotent stem cells," Nature Biotechnology, 25(10):1177-1181 (2007).
Nakagawa et al., "Generation of induced pluripotent stem cells without Myc from mouse and human fibroblasts," Nature Biotechnology, 26(1):101-106 (2008).
Sato et al. "Maintenance of pluripotency in human and mouse embryonic stem cells through activation of Wnt signaling by a pharmacological GSK-3-specific inhibitor," Nature Medicine, 10(1):5-63 (2004).
Takahashi et al., "Induction of Pluripotent Stem Cells from Mouse Embryonic and Adult Fibroblast Cultures by Defined Factors," Cell, 126(4):663-676 (2006).
Chien, et al., "WNTS and WNT receptors as therapeutic tools and targets in human disease processes", Front Biosci., 12: 448-457 (2011).
Gordon, et al., "Wnt Signaling: Multiple Pathways, Multiple Receptors, and Multiple Transcription Factors", The Journal of Biological Chemistry, 281(32): 22494-22433 (2006).
Lackie, et al., The Dictionary of Cell and Molecular Biology, Third Edition, 111 (1999).
Logan, et al., "The WNT signaling Pathway in Development and Disease", Annu. Rev. Cell Dev. Biol., 20: 781-810 (2004).
Nikolova, et al., "WNT-conditioned media differentially affect the proliferation and differentiation of cord blood-derived CD133+ cells in vitro", Differentiation, 75: 100-111 (2007).
Kim, et al., "Pluripotent stem cells inducted from adult neural stem cells by reprogramming with two factors", Nature, 1-6 (2008).
Kim, et al., "Oct4-Induced Pluripotency in Adult Neural Stem Cells", Cell, 136; 411-419 (2009).
Cowling, et al., "c-Myc Transforms Human Mammary Epithelial Cells through Repression of the Wnt Inhibitors DKK1 and SKRP1", Molecular and Cellular Biology, 27(14); 5135-5146 (2007).
Evans, et al., KLF4 Interacts with $^2$-Catenin/TCF4 and Blocks p300/CBP Recruitment by $^2$-Catenin, Molecular and Cellular Biology, 30(2): 372-381 (2009).
Li, et al., "SOX2 promotes tumor metastasis by stimulating epithelial-to-mesenchymal transition via regulation of WNT/$^2$-Catenin signal network", Cancer Letters, 335; 379-389 (2013).
Ogawa, et al., Synergistic action of Wnt and LIF in maintaining pluripotency of mouse ES cells, Biochemical and Biophysical Research Communications, 343; 159-166 (2006).
Sato, et al., "Maintenance of pluripotency in human and mouse embryonic stem cells through activation of Wnt signaling by a pharmacological GSK-3-specific inhibitor", Nature Medicine, 10(1): 55-63 (2004).
Anderson, et al. "The NOD mouse: a model of immune dysregulation," Annual Review of Immunology, 23:447-85 (2005).
Bach, et al., "The NOD mouse," Immunologic Research, 148: 285-286 (2008).
Bhat, et al., "Structural insights and biological effects of glycogen synthase kinase 3-specific inhibitor AR-A014418," The Journal of Biological Chemistry, 278, 45937-45945 (2003).
Brons, et al., "Derivation of pluripotent epiblast stem cells from mammalian embryos," Nature, 448: 191-195 (2007).
Buehr, et al., "Capture of authentic embryonic stem cells from rat blastocysts," Cell, 135: 1287-1298 (2008).
Cline, et al., "Effects of a novel glycogen synthase kinase-3 inhibitor on insulin-stimulated glucose metabolism in Zucker diabetic fatty (fa/fa) rats," Diabetes, 51:2903-2910 (2002).
Coughlan, et al., "Selective small molecule inhibitors of glycogen synthase kinase-3 modulate glycogen metabolism and gene transcription," Chemistry and Biology, 10, 793-803 (2000).
Cross, et al., "Selective small-molecule inhibitors of glycogen synthase kinase-3 activity protect primary neurons from death," Journal of Neurochemistry, 77, 94-102, (2001).
Frame, et al., "GSK3 takes centre stage more than 20 years after its discovery," Biochemical Journal, 359:1-16 (2001).
Guo, et al., "Klf4 reverts developmentally programmed restriction of ground state pluripotency" Development, 136(7): 1063-1069 (2009).
Hanna, et al. "Direct reprogramming of terminally differentiated mature B lymphocytes to pluripotency," Cell 133, 250-264 (2008).
Hanna, et al., "Metastable Pluripotent States in NOD-Mouse-Derived ESCs," Cell Stem Cell, 4:513-524(2009).
Huangfu, et al., "Induction of pluripotent stem cells from primary human fibroblasts with only Oct4 and Sox2," Nature Biotechnology, 26(11):1269-75 (2008).
Jaenisch, et al.,"Stem cells, the molecular circuitry of pluripotency and nuclear reprogramming," Cell 132, 567-582 (2008).
Jaenisch, Rudolf, Abstract "In vitro reprogramming of somatic cells into pluripotent ES-like cells" National Institutes of Health Grant No. 5 R37 HD045022-06 through 5 R37 HD045022-07, Funding Dates 2008 through 2009.
Jaenisch, Rudolf, Abstract "Nuclear Cloning and the Reprogramming of the Genome" National Institutes of Health Grant No. 5 R37 HD045022-01 through 5 R37 HD045022-05, Funding Dates 2003 through 2007.
Jaenisch, Rudolf, Abstract "Programming and reprogramming human cells" National Institutes of Health Grant No. 5 R01 CA084198-10, Funding Start Date 2009.
Jaenisch, Rudolf, Abstract "Genomic Imprinting and the Cloning of Mice" National Institutes of Health Grant Nos. 5 R01 CA084198-01 through 5 R01 CA084198-09 Funding Start Dates 2000 through 2008.
Jaenisch, Rudolf, Abstract "Epigenetics, stem cells, and cancer" National Institutes of Health Grant Nos. 5 RO1 CA087869-06 through 5 RO1 CA087869-09, Funding Dates 2006 through 2009.
Jaenisch, Rudolf, Abstract "DNA Methylation, Gene Regulation, and Cancer" National Institutes of Health Grant Nos. 5 RO1 CA087869-01 through 5 RO1 CA087869-05, Funding Dates 2001 through 2005.
Kikutani, et al., "The murine autoimmune diabetes model: NOD and related strains". Advances in Immunology, 51: 285-322 (2002).
Leost, et al., "Paullones are potent inhibitors of glycogen synthase kinase-3b and cyclin-dependent kinase 5/p25," European Journal of Biochemistry, 267, 5983-5994 (2000).
Li, et al., "Germline competent embryonic stem cells derived from rat blastocysts," Cell, 135: 1299-1310 (2008).
Li, et al., "Generation of rat and human induced pluripotent stem cells by combining genetic reprogramming and chemical inhibitors," Cell Stem Cell, 4: 16-19 (2009).
Liao, et al., "Generation of induced pluripotent stem cell lines from adult rat cells," Cell Stem Cell, 4: 11-15 (2009).
Lyssiotis, et al. "Reprogramming of murine fibroblasts to iPS cells: chemical complementation of Klf4," (Submitted 2009).
Makino S, et al., "Breeding of a non-obese, diabetic strain of mice," Jikken Dobutsu, 29 (1): 1-13 (1980).
Markoulaki, et al., "Transgenic mice with defined combinations of drug-inducible reprogramming factors," Nature Biotechnology, 27: 169-171 (2009).
Mikels, et al., "Wnts as ligands:processing, secretion and reception," Oncogene, 25: 7461-7468 (2006).
Mikkelson, et al., "Dissecting direct reprogramming through integrative genomic analysis," Nature, 454(7200):49-55 (2008).
Nagafuchi, et al., "Establishment of an embryonic stem (ES) cell line derived from a non-obese diabetic (NOD) mouse: in vivo differentia-

(56) References Cited

OTHER PUBLICATIONS tion into lymphocytes and potential for germ line transmission," FEBS Letters, 455:101-104 (1999).

Polychronopoulos, et al., "*Structural basis for the synthesis of indirubins as potent and selective inhibitors of glycogen synthase kinase-3 and cyclin-dependent kinases*," Journal of Medicinal Chemistry, 47, 935-946, (2004).

Rossant, J. "*Stem cells and early lineage development,*" Cell 132, 527-531 (2008).

Schultz, et al., "*Paullones, a series of cyclin-dependent kinase inhibitors: synthesis, evaluation of CDK1/Cyclin B inhibition, an in vitro antitumor activity,*" Journal of Medicinal Chemistry, 42: 2909-2929 (1999).

Shi, Y., et al., "*A combined chemical and genetic approach for the generation of induced pluripotent stem cells,*" Cell Stem Cell 2, 525-528 (2008).

Shi, Y., et al., "*Introduction of Pluripotent Stem Cells from Mouse Embryonic Fibroblasts by Oct4 and Klf4 with small-molecule compounds,*" Cell Stem Cell, 3:568-574, 2008.

Silva, et al., "*Promotion of reprogramming to ground state pluripotency by signal inhibition,*" PloS Biology, 6: e253 (2008a).

Silva, et al., "*X-chromosome inactivation and epigenetic fluidity in human embryonic stem cells,*" PNAS, 105: 4820-4825 (2008b).

Smith, et al., *3-Anilino-4-arylmaleimides: potent and selective inhibitors of glycogen synthase kinase-3 (GSK-3)*, Bioorganic and Medicinal Chemistry Letter, 11, 635-639, (2001).

Wagman, et al. "*Discovery and development of GSK3 inhibitors for the treatment of type 2 diabetes,*", Current Pharmaceutical Design, 10(10):1105-1037 (2004).

Wakayama, et al., "*Full-term development of mice from enucleated oocytes injected with cumulus cell nuclei,*" Nature 394, 369-374 (1998).

Wernig, et al., "*In vitro reprogramming of fibroblasts into a pluripotent ES-cell-like state,*" Nature, 448: 318-324 (2007).

Ying, et al., "*BMP induction of Id proteins suppresses differentiation and sustains embryonic stem cell self-renewal in collaboration with STAT3,*" Cell, 115: 281-292 (2003).

Ying, et al., "*The ground state of embryonic stem cell self-renewal,*" Nature, 453: 519-523 (2008).

Zaharevitz, et al., "*Discovery and Initial Characterization of the Paullones, a Novel Class of Small-Molecule Inhibitors of Cyclin-dependent Kinases,*"Cancer Research, 59, 2566-2569, (1999).

International Search Report for International Application PCT/US2010/032435, dated Feb. 28, 2011.

Non-Final Office Action for U.S. Appl. No. 12/767,606 (listed on SB-08 as US 2011-0088107), dated Sep. 11, 2012.

Final Office Action for U.S. Appl. No. 12/767,606 (listed on SB-08 as US 2011-0088107), dated May 15, 2013.

* cited by examiner

A. Timeline of Experiment
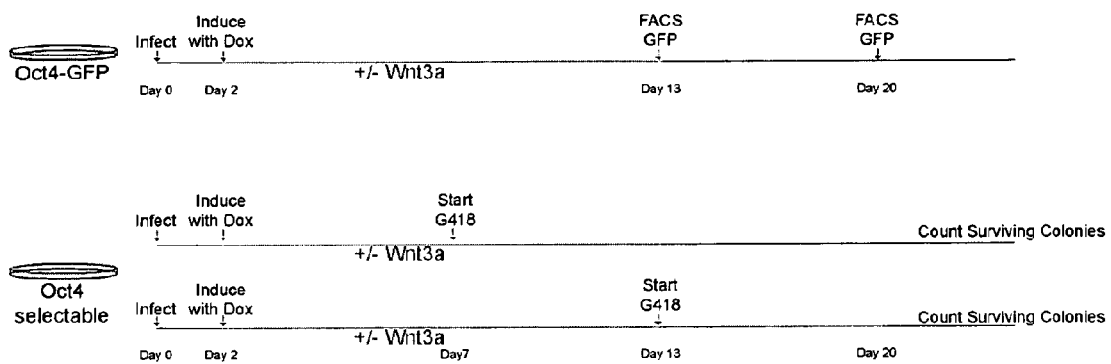
B. Wnt3a promotes iPS cell formation in cells over-expressing Oct4, Sox2, Klf4 and c-Myc
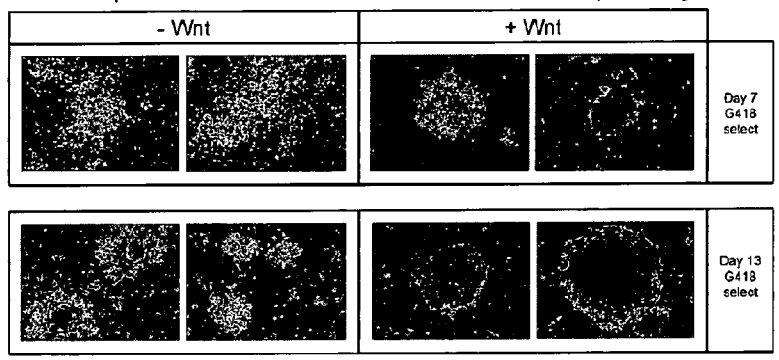
C. Wnt3a promotes iPS cell formation in cells over-expressing Oct4, Sox2, Klf4 (no c-Myc)
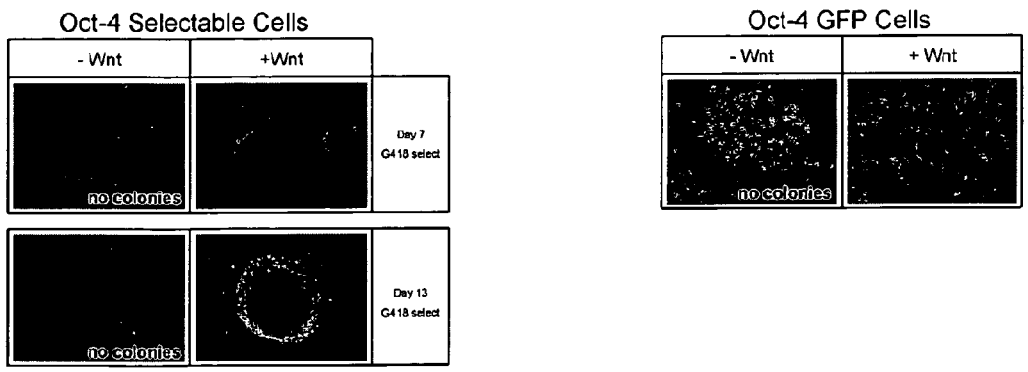
Figure 4

WNT PATHWAY STIMULATION IN REPROGRAMMING SOMATIC CELLS WITH NUCLEAR REPROGRAMMING FACTORS

CROSS-REFERENCE TO RELATED APPLICATIONS

This application is a U.S. national stage application filed under 35 U.S.C. §371 of International Application PCT/US2008/010249, filed Aug. 29, 2008, which claims the benefit of priority to U.S. Provisional Patent Application 60/967,028, filed Aug. 31, 2007, and U.S. Provisional Patent Application 61/188,190, filed Aug. 6, 2008, both of which are incorporated herein by reference in their entirety. International Application No. PCT/US2008/010249 was published under PCT Article 21(2) in English.

GOVERNMENTAL FUNDING

The invention described herein was supported, in whole or in part, by grants 5-RO1-HDO45022, 5-R37-CA084198, and 5-RO1-CA087869 to RJ and by NIH grant HG002668 from the National Institutes of Health. The United States government has certain rights in the invention.

BACKGROUND OF THE INVENTION

Stem cells are cells that are capable of self-renewal and of giving rise to more differentiated cells. Embryonic stem (ES) cells can differentiate into the multiple specialized cell types that collectively comprise the body. In addition to being of immense scientific interest, the property of pluripotency gives human ES cells great clinical promise for applications in regenerative medicine such as cell/tissue replacement therapies for disease.

Several different methods are currently used to obtain ES cells. In one method, an ES cell line is derived from the inner cell mass of a normal embryo in the blastocyst stage (See U.S. Pat. Nos. 5,843,780 and 6,200,806, Thompson, J. A. et al. Science, 282:1145-7, 1998). A second method for creating pluripotent ES cells utilizes somatic cell nuclear transfer (SCNT). In this technique, the nucleus is removed from a normal egg, thus removing the genetic material. The nucleus of a donor diploid somatic cell is introduced directly into the enucleated oocyte, e.g., by micromanipulation, or the donor diploid somatic cell is placed next to the enucleated egg and the two cells are fused. The resulting cell has the potential to develop into an early embryo from which the portion containing the stem cell producing inner cell mass can be obtained. In a third method, the nucleus of a human cell is transplanted into an enucleated animal oocyte of a species different from the donor cell. See, e.g., U.S. Pat. Pub. No. 20010012513. The resultant chimeric cells are used for the production of pluripotent ES cells, in particular human-like pluripotent ES cells. Disadvantages of this technique are that these chimeric cells may contain unknown viruses and retain the mitochondria of the animal species.

The traditional ES cell isolation methods suffer from several limitations when applied to generating human ES cells. These include ethical controversies associated with the source of the cells as well as technical challenges. A significant limitation to the productive utilization of ES cells for clinical applications is the difficulty associated with generating ES cells that are genetically matched to individual patients. There exists a significant need for alternative methods of generating pluripotent cells.

SUMMARY OF THE INVENTION

The present invention provides compositions and methods for reprogramming somatic cells to a less differentiated state. In certain embodiments the compositions and methods permit reprogramming of somatic cells to pluripotent, embryonic stem cell-like cells ("ES-like cells").

In one aspect, the invention provides a method of reprogramming a somatic mammalian cell comprising culturing the cell in the presence of an extracellular signaling molecule so that the cell becomes reprogrammed.

In one aspect the invention provides a method of reprogramming a somatic mammalian cell comprising culturing the cell in Wnt conditioned cell culture medium so that the cell becomes reprogrammed. In certain embodiments the method comprises culturing the somatic cell so that the cell is induced to become pluripotent. In certain embodiments the Wnt conditioned cell culture medium comprises Wnt3a conditioned medium (Wnt3a-CM).

In another aspect the invention provides a method of reprogramming a somatic mammalian cell comprising contacting the cell with an agent that increases the activity of a Wnt pathway so that the cell is induced to become pluripotent. In some embodiments the agent is a soluble, biologically active Wnt protein, e.g., a Wnt3a protein. In some embodiments the agent is selected from the group consisting of: (i) small molecules that mimic the effect of Wnt3a conditioned medium or soluble, biologically active Wnt proteins, e.g., by interacting with cell receptor(s) for Wnt; (ii) agents that modulate the interaction between β-catenin and a member of the TCF/LEF family and/or modulate the expression or activity of a member of the TCF/LEF family; (iii) agents that inhibit expression or activity of an endogenous inhibitor of the Wnt pathway.

The invention provides somatic cells reprogrammed using the inventive methods.

Cell culture media containing a Wnt3a activator and an additional reprogramming agent capable of substituting for engineered expression of Oct4, Klf4, and/or Sox2 (or any combination thereof) are additional aspects of this invention. Further aspects of the invention are (1) a composition comprising: (i) a cell that has been modified to increase its expression of Oct4, Klf4, and/or Sox2, or any subset of these; and (ii) a Wnt pathway modulator, e.g., a Wnt pathway activator; (2) a composition comprising: (i) a cell that has been modified to increase its expression or intracellular level of one or more reprogramming factors, wherein the reprogramming factor(s) is/are optionally selected from Oct4, Klf4, and/or Sox2, or any subset of these; and (ii) Wnt conditioned medium; (3) a composition comprising: (i) a cell that has been modified to increase its expression or intracellular level of one or more reprogramming factors, wherein the reprogramming factor(s) is/are optionally selected from Oct4, Nanog, Lin28 and/or Sox2, or any subset of these; and (ii) a Wnt pathway activator; and (4) a composition comprising: (i) a cell that has been modified to increase its expression or intracellular level of one or more reprogramming factors, wherein the reprogramming factor(s) is/are optionally selected from Oct4, Nanog, Lin28 and/or Sox2, or any subset of these; and (ii) Wnt conditioned medium.

The invention also provides methods for identifying an agent that reprograms somatic cells to a less differentiated state and/or contributes to such reprogramming in combination with one or more other agents. In certain of the methods, somatic cells are contacted with an agent that increases Wnt pathway activity and a candidate agent. Cells are assessed for pluripotency characteristics. The presence of at least a subset of pluripotency characteristics indicates that the agent is capable of reprogramming somatic cells to a less-differentiated state. The agents identified by the present invention can then by used to reprogram somatic cells by contacting somatic cells with the agents.

The present invention further provides methods for treating a condition in an individual in need of treatment for a condition. In certain embodiments, somatic cells are obtained from the individual and reprogrammed by the methods of the invention. The reprogrammed cells may be expanded in culture. Pluripotent reprogrammed cells (which refers to the original reprogrammed cells and/or their progeny that retain the property of pluripotency) are maintained under conditions suitable for the cells to develop into cells of a desired cell type or cell lineage. In some embodiments, the cells are differentiated in vitro using protocols, such as those known in the art. The reprogrammed cells of a desired cell type are introduced into the individual to treat the condition. In certain embodiments, the somatic cells obtained from the individual contain a mutation in one or more genes. In these instances, in certain embodiments the somatic cells obtained from the individual are first treated to repair or compensate for the defect, e.g., by introducing one or more wild type copies of the gene(s) into the cells such that the resulting cells express the wild type version of the gene. The cells are then introduced into the individual.

In certain embodiments, the somatic cells obtained from the individual are engineered to express one or more genes following their removal from the individual. The cells may be engineered by introducing a gene or expression cassette comprising a gene into the cells. The introduced gene may be one that is useful for purposes of identifying, selecting, and/or generating a reprogrammed cell. In certain embodiments the introduced gene(s) contribute to initiating and/or maintaining the reprogrammed state. In certain embodiments the expression product(s) of the introduced gene(s) contribute to producing the reprogrammed state but are dispensable for maintaining the reprogrammed state.

In certain other embodiments, methods of the invention can be used to treat individuals in need of a functional organ. In the methods, somatic cells are obtained from an individual in need of a functional organ, and reprogrammed by the methods of the invention to produce reprogrammed somatic cells. Such reprogrammed somatic cells are then cultured under conditions suitable for development of the reprogrammed somatic cells into a desired organ, which is then introduced into the individual.

In further summary, the invention provides a method of reprogramming a somatic mammalian cell comprising contacting the somatic mammalian cell with an agent that modulates a Wnt pathway so that the somatic mammalian cell becomes reprogrammed. In certain embodiments of the invention the method comprises reprogramming the somatic mammalian cell to a pluripotent state. In certain aspects, the invention provides improvements in methods of generating induced pluripotent stem (iPS) cells. For example, in certain aspects the invention enhances reprogramming somatic cells to pluripotency that have not been engineered to express c-Myc. In certain aspects, the inventive methods facilitate generating homogenous ES-like colonies. In some embodiments, the inventive methods enhance formation of homogenous, ES-like colonies without imposing a selection step that requires genetic modification of the initial somatic cells.

In certain embodiments of the invention, the method comprises culturing the cell in Wnt-conditioned medium. In certain embodiments, the method comprises culturing the cell in Wnt3a-conditioned medium. In certain embodiments, the cell is a human cell. In certain embodiments the cell is a mouse cell. In certain embodiments, the cell is a non-human primate cell. In certain embodiments, the somatic mammalian cell is a terminally differentiated cell. In certain embodiments the cell is a fibroblast or immune system cell (e.g., B or T cell). In certain embodiments, the somatic mammalian cell is not a terminally differentiated cell. For example, the somatic mammalian cell may be a precursor cell, e.g., a neural precursor or hematopoietic precursor cell. In certain embodiments, the method is practiced in vitro. In certain embodiments, contacting the cell comprises culturing the cell in culture medium containing the agent. In certain embodiments, contacting comprises culturing the cell in culture medium comprising the agent for at least 10 days. In certain embodiments, contacting comprises culturing the cell in culture medium comprising the agent for at least 12 or at least 15 days or at least 20 days. In certain embodiments, the somatic cell is genetically modified to contain a nucleic acid sequence encoding a selectable marker, operably linked to a promoter for an endogenous pluripotency gene thereby allowing selection of cells that have been reprogrammed to pluripotency while in other embodiments the somatic cell is not genetically modified to contain a nucleic acid sequence encoding a selectable marker operably linked to a promoter for an endogenous pluripotency gene thereby allowing selection of cells that have been reprogrammed to pluripotency. In certain embodiments, the somatic cell is modified to express or contain at least one reprogramming factor at levels greater than normally present in somatic cells of that type. In some embodiments, the reprogramming factor is Oct4. In some embodiments, the reprogramming factor is Sox2. In some embodiments the reprogramming factor is Klf4. In some embodiments the reprogramming factor is Nanog. In some embodiments the reprogramming factor is Lin28. In some embodiments the reprogramming factor(s) are Oct4 and Sox2. In some embodiments the reprogramming factor(s) are Oct4, Sox2, and Klf4. In certain embodiments, the somatic cell is not genetically modified to express c-Myc at levels greater than normally present in somatic cells of that cell type. In certain embodiments, the cell is also contacted with a second agent that modulates the Wnt pathway. In certain embodiments, the somatic cell is cultured in medium containing exogenous soluble, biologically active Wnt protein. In certain embodiments, the Wnt protein is Wnt3a protein. In certain embodiments, the method further comprises confirming that the reprogrammed cell is pluripotent. In certain embodiments, the method is practiced on a population of cells and the method further comprises separating cells that are reprogrammed to a pluripotent state from cells that are not reprogrammed to a pluripotent state. In certain embodiments, the method further comprises administering the reprogrammed cell to a subject. In certain embodiments, the method further comprises differentiating the cell to a desired cell type in vitro after reprogramming the cell. In certain embodiments, the method further comprises administering the differentiated cell to a subject.

The invention also provides a method of treating an individual in need thereof comprising: (a) obtaining somatic cells from the individual; (b) reprogramming at least some of the somatic cells by a method comprising contacting the somatic mammalian cells with an agent that modulates the Wnt pathway (e.g., a Wnt pathway activator); and (c) administering at least some of the reprogrammed cells to the individual, optionally after differentiating the cells into one or more desired cell types. In some embodiments, the individual is a human. In some embodiments, the method is practiced on a population of cells and further comprises separating cells that are reprogrammed to a pluripotent state from cells that are not reprogrammed to a pluripotent state. In some embodiments, the method further comprises differentiating the cell in vitro and, optionally, administering the differentiated cell to an individual in need of treatment for a condition for which cell therapy is of use. For example, cells may be differentiated along a desired cell lineage such as a neural lineage, a muscle lineage, etc.

The invention further provides composition comprising (i) a somatic mammalian cell that has been modified or treated so that it expresses or contains at least one reprogramming factor at levels greater than would be the case without such modification or treatment; and (ii) an agent that increases activity of a Wnt pathway and contributes to reprogramming the somatic cell to a pluripotent state. In certain embodiments, the agent is Wnt3a protein. In certain embodiments, the agent is a small molecule.

The invention further provides a method of identifying an agent useful for modulating the reprogramming of mammalian somatic cells to a pluripotent state comprising: (a) culturing a population of mammalian somatic cells in medium containing an agent that modulates activity of a Wnt pathway and a candidate agent; and (b) determining, after a suitable period of time, whether cells having one or more characteristics of ES cells are present after maintaining the cells and their progeny in culture for a suitable time period, wherein the candidate agent is identified as being useful for modulating the reprogramming of mammalian somatic cells to a pluripotent state if cells having one or more characteristics of ES cells are present at levels different than would be expected had the medium not contained the candidate agent.

In certain embodiments, the characteristics are selected from: colony morphology, expression of an endogenous gene expressed selectively by ES cells, expression of a detectable marker operably linked to expression control sequences of a gene expressed selectively by ES cells, ability to differentiate into cells having characteristics of endoderm, mesoderm, and ectoderm when injected into immunocompromised mice, and ability to participate in formation of chimeras that survive to term. In certain embodiments, the cells have been modified to express at least one reprogramming factor. In certain embodiments, the medium is Wnt-conditioned medium.

In certain embodiments, the medium is Wnt3a-conditioned medium. In certain embodiments, the agent that modulates activity of a Wnt pathway is Wnt3a protein. In certain embodiments, the agent that modulates activity of a Wnt pathway is a small molecule. In certain embodiments, the candidate agent is a small molecule. In certain embodiments, the method comprises identifying an agent useful for enhancing the reprogramming of mammalian somatic cells, wherein the candidate agent is identified as being useful for enhancing the reprogramming of mammalian somatic cells to a pluripotent state if cells having one or more characteristics of ES cells are present at levels greater than would be expected had the medium not contained the candidate agent. In certain embodiments, step (b) comprises determining whether cell colonies having one or more characteristics of ES cell colonies are present after maintaining the cells and their progeny in culture for a suitable time period, wherein the candidate agent is identified as being useful for modulating the reprogramming of mammalian somatic cells to a pluripotent state if cell colonies having one or more characteristics of ES cell colonies are present at levels different than would be expected had the medium not contained the candidate agent. In certain embodiments, the cells express at least one reprogramming factor.

The invention also provides a method of identifying an agent useful for reprogramming mammalian somatic cells to a pluripotent state comprising: (a) contacting a population of mammalian somatic cells with an agent that increases Wnt pathway activity and a candidate agent; (b) maintaining the cells in a cell culture system for a suitable period of time; and (c) determining whether cells having one or more characteristics of ES cells are present in said culture system, wherein the agent is identified as being useful for reprogramming mammalian somatic cells to an ES-like state if cells having one or more characteristics of ES cells are present at levels greater than would be expected had the cells not been contacted with the candidate agent.

In certain embodiments of the invention, the characteristics are selected from: colony morphology, expression of an endogenous gene expressed selectively by ES cells, expression of a detectable marker operably linked to expression control sequences of a gene expressed selectively by ES cells, ability to differentiate into cells having characteristics of endoderm, mesoderm, and ectoderm when injected into immunocompromised mice, and ability to participate in formation of chimeras that survive to term.

In certain embodiments, the agent that increases Wnt pathway activity is Wnt3a protein. In certain embodiments, the candidate agent is a small molecule. In certain embodiments, the cells express at least one reprogramming factor. In certain embodiments, step (b) comprises determining whether cell colonies having one or more characteristics of ES cell colonies are present after maintaining the cells and their progeny in culture for a suitable time period, wherein the candidate agent is identified as being useful for modulating the reprogramming of mammalian somatic cells to a pluripotent state if cell colonies having one or more characteristics of ES cell colonies are present at levels different than would be expected had the medium not contained the candidate agent.

The invention also provides a method of reprogramming a somatic mammalian cell comprising culturing the cell in the presence of an extracellular signaling molecule so that the cell becomes reprogrammed. In certain embodiments, said extracellular signaling molecule is a molecule whose binding to an extracellular domain of a cellular receptor initiates or modifies a signal transduction pathway within the cell. In certain embodiments, the signal transduction pathway is the Wnt pathway.

The invention also provides a method of identifying a Wnt pathway modulator useful for modulating the reprogramming of mammalian somatic cells to a pluripotent state comprising: (a) culturing a population of mammalian somatic cells in medium containing the Wnt pathway modulator; (b) determining, after a suitable period of time, whether cells having one or more characteristics of ES cells are present after maintaining the cells and their progeny in culture for a suitable time period, wherein the Wnt pathway modulator is identified as being useful for modulating the reprogramming of mammalian somatic cells to a pluripotent state if cells having one or more characteristics of ES cells are present at levels different than would be expected had the medium not contained the Wnt pathway modulator.

In certain embodiments, the method comprises (i) testing at least 10 Wnt pathway modulators; and (ii) identifying one or more of the Wnt pathway modulators as having significantly greater effect on reprogramming speed or efficiency than at least 50% of the other Wnt pathway modulators tested. In certain embodiments, the method comprises testing at least 20, at least 50, or at least 100 Wnt pathway modulators. In some embodiments, the method comprises identifying one or more of the Wnt pathway modulators as having significantly greater effect on reprogramming speed or efficiency than at least 75%, or at least 90% of the other Wnt pathway modulators tested. In certain embodiments, the Wnt pathway modulators tested are small molecules. In certain embodiments, the Wnt pathway modulators tested are structurally related. For example, they may be members of a set of compounds, e.g., a combinatorial compound library, synthesized based on a common core structure or they may be derivatives obtained by modifying a core structure or lead compound such as by making substitutions or additions at one or more positions. In certain embodiments, the Wnt pathway modulator is identified as being useful for increasing the speed or efficiency of reprogramming cells to an ES-like state if, after a suitable time period, cells having one or more characteristics of ES cells are present in numbers greater than would be expected had the medium not contained the Wnt pathway modulator. In certain embodiments, the Wnt pathway modulator is identified as being useful for increasing the speed or efficiency of reprogramming cells to a pluripotent state if, after a suitable time period, cell colonies having one or more characteristics of ES cell colonies, are present in numbers greater than would be expected had the medium not contained the Wnt pathway modulator. For example, the methods may result in an increased percentage of colonies having features of ES cell colonies and/or the colonies may be more homogenous than would be the case in the absence of the Wnt pathway modulator.

The invention further provides a cell culture composition comprising: (a) cell culture medium containing a Wnt pathway modulator; and (b) a plurality of mammalian somatic cells, wherein (i) the cells are genetically modified or transiently transfected to express one or more reprogramming factors; (ii) the cells are genetically modified to contain a nucleic acid sequence encoding a selectable marker, operably linked to a promoter for an endogenous pluripotency gene, thereby allowing selection of cells that have been reprogrammed to pluripotency; or (iii) the cell culture medium contains one or more small molecules, nucleic acids, or polypeptides that substitute for a reprogramming factor other than c-Myc.

In certain embodiments, the cell culture medium comprises Wnt-3a CM. In certain embodiments, the medium contains a small molecule that modulates the Wnt pathway.

In certain embodiments, the one or more reprogramming factors are selected from: Oct4, Nanog, Sox2, Lin28, and Klf4. The invention further provides a composition comprising: an iPS cell and an agent that modulates, e.g., activates, the Wnt pathway. In certain embodiments the agent that activates the Wnt pathway is Wnt3a protein. In certain embodiments the agent that activates the Wnt pathway is a small molecule.

In certain embodiments, the invention provides use of an agent that modulates a Wnt pathway in the manufacture of a medicament for reprogramming a somatic mammalian cell.

It is contemplated that all embodiments described herein are applicable to the various aspects of the invention. It is also contemplated that the various embodiments of the invention and elements thereof can be combined with one or more other such embodiments and/or elements whenever appropriate.

BRIEF DESCRIPTION OF THE DRAWINGS

FIG. 4. (a) Timeline of initial experiments showing ability of Wnt3a conditioned medium to promote generation of iPS cells. Expression of the pluripotency-inducing factors was induced on day 2. Expression of GFP and colony formation were assessed as indicated (b). Wnt3a promotes iPS cell formation in cells over-expressing Oct4, Sox2, Klf4 and c-Myc; FIG. 4C. Wnt3a promotes iPS cell formation in cells over-expressing Oct4, Sox2, Klf4 without engineered expression of c-Myc; (c) Wnt3a promotes iPS cell formation in cells over-expressing Oct4, Sox2, Klf4 without engineered expression of c-Myc.

DETAILED DESCRIPTION OF THE INVENTION

Introduction and Definitions

Figure 1:
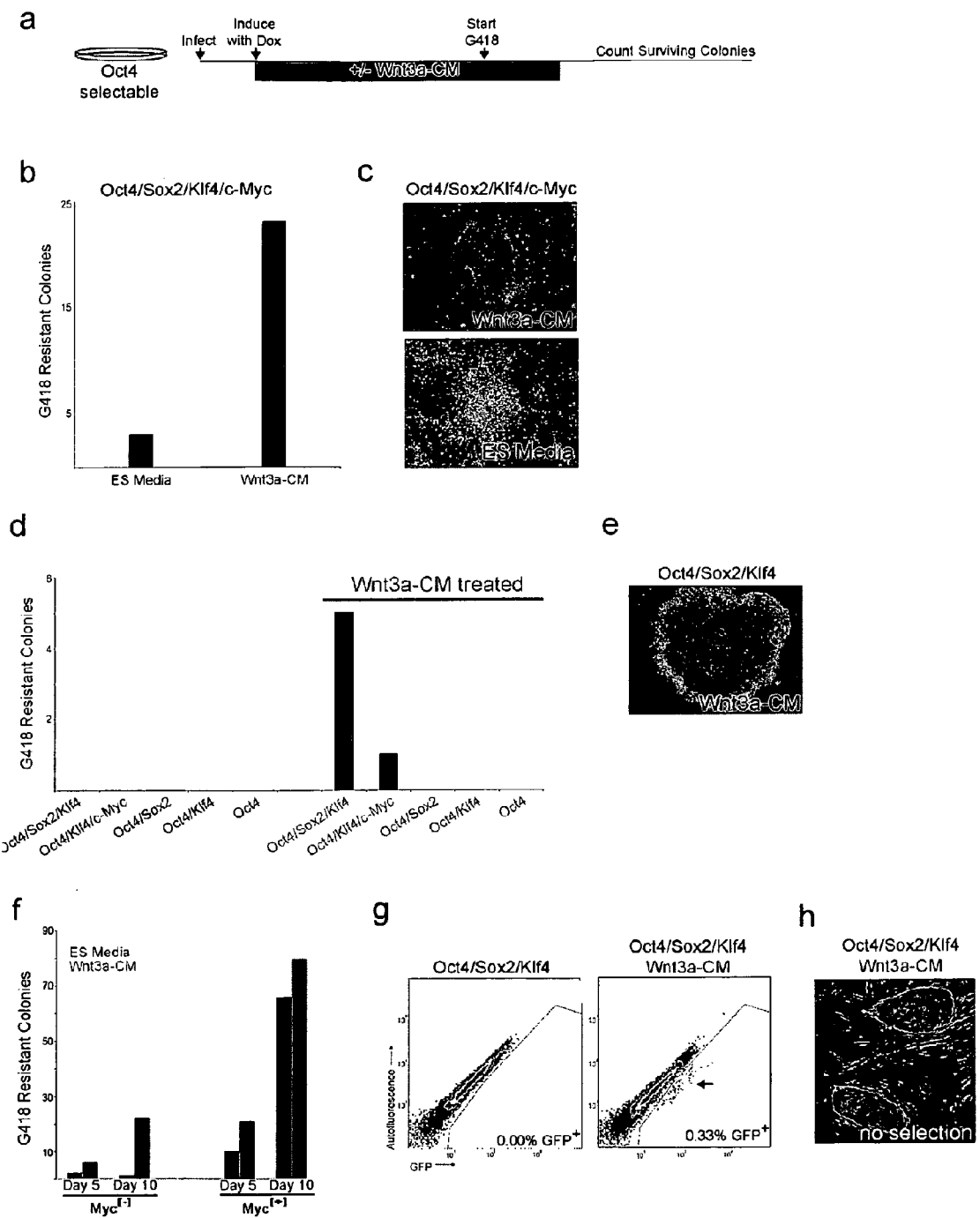
FIG. 1. Wnt3a promotes epigenetic reprogramming. a. Schematic representation of the experimental time-line. MEFs were infected with DOX-inducible lentivirus, split into cultures with and without Wnt3-CM treatment, and then induced with DOX (day 0). G418 selection was initiated at fixed time points after induction and Wnt3a-CM treatment was maintained for 7 days of selection. DOX and G418 were maintained until resistant colonies were assessed. b. G418-resistant colony counts from MEFs overexpressing Oct4/Sox2/Klf4/c-Myc in standard ES cell media or with Wnt3a-CM treatment. c. Phase images of G418 resistant colonies formed with and without Wnt3a-CM treatment. d. G418-resistant colony counts from MEFs infected with different combination of reprogramming factors in the presence and absence of Wnt3a-CM. G418 resistant colonies emerged without c-Myc transduction in the presence of Wnt3a-CM. e. Phase image of Myc[−] G418 resistant colony formed with Wnt3a-CM treatment. In this experiment, no colonies were observed for Myc[−] cells in the absence of Wnt3a-CM. f. G418-resistant colony counts from MEFs over-expressing Oct4/Sox2/Klf4 (Myc[−]) or Oct4/Sox2/Klf4/c-Myc (Myc[+]) in the presence (red bars) and absence (gray bars) of Wnt3a-CM. G418 selection was initiated on day 5 or day 10 post-induction as indicated and colonies (in a 32-cm$^2$ area) were assessed on day 20. g. Scatter plots comparing GFP intensity to autofluorescence, using flow cytometry, in Oct4-GFP cells on day 20 post-induction of Oct4/Sox2/Klf4, reveal a GFP expressing population of cells (indicated with an arrow) only with Wnt3a-CM treatment. h. Phase image of GFP expressing Myc[−] cells derived with Wnt3a-CM treatment and without any genetic selection.

The present invention relates to compositions and methods for reprogramming somatic cells, e.g., for reprogramming somatic cells to pluripotency in vitro. The invention provides methods for reprogramming somatic cells to a less differentiated state. The resulting cells are referred to herein as "reprogrammed somatic cells" ("RSC") herein, or in some embodiments as induced pluripotent stem (iPS) cells if reprogrammed to a pluripotent state. The term "somatic cell" refers to any cell other than a germ cell, a cell present in or obtained from a pre-implantation embryo, or a cell resulting from proliferation of such a cell in vitro. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming cells to a less differentiated state are performed in vitro, i.e., they are practiced using isolated somatic cells maintained in culture.

The invention encompasses the recognition that naturally occurring signaling molecules that modulate the expression of endogenous ES cell transcription factors are promising candidates for soluble agents that enhance reprogramming. The invention also encompasses the recognition that modulating the biological pathways with which such naturally occurring signaling molecules interact is of use to enhance (e.g., increase speed and/or efficiency of) reprogramming. The invention also encompasses the recognition that agents (whether naturally occurring or synthetic, e.g., small molecules) that modulate the biological pathways with which such naturally occurring signaling molecules interact, are promising candidates for soluble agents that enhance reprogramming.

As described in more detail below, certain embodiments of the invention are based at least in part on the recognition that modulating, e.g., activating, the Wnt pathway is of use in reprogramming somatic cells. Certain of the methods comprising increasing activity of the Wnt pathway in somatic cells such that at least some of the cells become reprogrammed, e.g., to a pluripotent state. Certain of the methods comprise culturing somatic cells in Wnt conditioned medium such that at least some of the cells become reprogrammed, e.g., to a pluripotent state.

Reprogramming, as used herein, refers to a process that alters or reverses the differentiation state of a somatic cell. The cell can be either partially or terminally differentiated prior to reprogramming. Reprogramming encompasses complete reversion of the differentiation state of a somatic cell to a pluripotent state. As known in the art, a "pluripotent" cell has the ability to differentiate into or give rise to cells derived from all three embryonic germ layers (endoderm, mesoderm and ectoderm) and typically has the potential to divide in vitro for a long period of time, e.g., greater than one year or more than 30 passages. ES cells are an example of pluripotent cells. Reprogramming also encompasses partial reversion of the differentiation state of a somatic cell to a multipotent state. A "multipotent" cell is a cell that is able to differentiate into some but not all of the cells derived from all three germ layers. Thus, a multipotent cell is a partially differentiated cell. Adult stem cells are multipotent cells. Adult stem cells include, for example, hematopoietic stem cells and neural stem cells. Reprogramming also encompasses partial reversion of the differentiation state of a somatic cell to a state that renders the cell more susceptible to complete reprogramming to a pluripotent state when subjected to additional manipulations such as those described herein. Such contacting may result in expression of particular genes by the cells, which expression contributes to reprogramming. In certain embodiments of the invention, reprogramming of a somatic cell causes the somatic cell to assume a pluripotent, ES-like state. The resulting cells are referred to herein as reprogrammed pluripotent somatic cells or induced pluripotent stem (iPS) cells.

Reprogramming involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods of the invention may also be of use for such purposes. Certain of the compositions and methods of the present invention contribute to establishing the pluripotent state. The methods may be practiced on cells that fully differentiated and/or restricted to giving rise only to cells of that particular type, rather than on cells that are already multipotent or pluripotent.

Somatic cells are treated in any of a variety of ways to cause reprogramming according to the methods of the present invention. The treatment can comprise contacting the cells with one or more agent(s) that contribute to reprogramming ("reprogramming agent"). Such contacting may be performed by maintaining the cell in culture medium comprising the agent(s). In some embodiments the somatic cells are genetically engineered. The somatic cell may be genetically engineered to express one or more reprogramming agents as described further below.

In the methods of the present invention somatic cells may, in general, be cultured under standard conditions of temperature, pH, and other environmental conditions, e.g., as adherent cells in tissue culture plates at 37° C. in an atmosphere containing 5-10% $CO_2$. The cells and/or the culture medium are appropriately modified to achieve reprogramming as described herein. In certain embodiments, the somatic cells are cultured on or in the presence of a material that mimics one or more features of the extracellular matrix or comprises one or more extracellular matrix or basement membrane components. In some embodiments Matrigel™ is used. Other materials include proteins or mixtures thereof such as gelatin, collagen, fibronectin, etc. In certain embodiments of the invention the somatic cells are cultured in the presence of a feeder layer of cells. Such cells may, for example, be of murine or human origin. They may be irradiated, chemically inactivated by treatment with a chemical inactivator such as mitomycin c, or otherwise treated to inhibit their proliferation if desired. In other embodiments the somatic cells are cultured without feeder cells.

Generating pluripotent or multipotent cells by somatic cell reprogramming using the methods of the present invention has a number of advantages. First, the methods of the present invention allow one to generate autologous pluripotent cells, which are cells specific to and genetically matched with an individual. The cells are derived from somatic cells obtained from the individual. In general, autologous cells are less likely than non-autologous cells to be subject to immunological rejection. Second, the methods of the present invention allow the artisan to generate pluripotent cells without using embryos, oocytes, and/or nuclear transfer technology. Applicants' results demonstrate that (i) somatic cells can be reprogrammed to an ES-like state without the need to engineer the cells to express an oncogene such as c-Myc; and (ii) reprogramming of somatic cells can at least in part be effected by means other than engineering the cells to express reprogramming factors, i.e., by contacting the cells with a reprogramming agent other than a nucleic acid or viral vector capable of being taken up and causing a stable genetic modification to the cells. In particular, the invention encompasses the recognition that extracellular signaling molecules, e.g., molecules that when present extracellularly bind to cell surface receptors and activate intracellular signal transduction cascades, are of use to reprogram somatic cells. The invention further encompasses the recognition that activation of such signaling pathways by means other than the application of extracellular signaling molecules is also of use to reprogram somatic cells. In addition, the methods of the present invention enhanced the formation of colonies of ES-like cells that were detectable based on morphological criteria, without the need to employ a selectable marker. The present disclosure thus reflects several fundamentally important advances in the area of in vitro somatic cell reprogramming technology. While certain aspects of the invention are exemplified herein using Wnt pathway signaling, the methods of the invention encompass activation of other signaling pathways for purposes of reprogramming somatic cells.

Definitions of certain terms useful for understanding aspects of the invention are presented below:

"Agent" as used herein means any compound or substance such as, but not limited to, a small molecule, nucleic acid, polypeptide, peptide, drug, ion, etc.

A "cell culture medium" (also referred to herein as a "culture medium" or "medium") is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Some non-limiting examples are provided herein.

"Cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

"Expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

A "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

"Identity" refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, *Proc. Natl. Acad. Sci. USA* 87:22264-2268, 1990) modified as in Karlin and Altschul, *Proc. Natl. Acad. Sci. USA* 90:5873-5877, 1993 is incorporated into the NBLAST and XBLAST programs of Altschul et al. (Altschul, et al., *J. Mol. Biol.* 215:403-410, 1990). To obtain gapped alignments for comparison purposes, Gapped BLAST is utilized as described in Altschul et al. (Altschul, et al. *Nucleic Acids Res.* 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

"Isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated". An "isolated cell" is a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "gene whose function is associated with pluripotency", as used herein, refers to a gene whose expression under normal conditions (e.g., in the absence of genetic engineering or other manipulation designed to alter gene expression) occurs in and is typically restricted to pluripotent stem cells, and is crucial for their functional identity as such. It will be appreciated that the polypeptide encoded by a gene functionally associated with pluripotency may be present as a maternal factor in the oocyte. The gene may be expressed by at least some cells of the embryo, e.g., throughout at least a portion of the preimplantation period and/or in germ cell precursors of the adult.

"Modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

The term "pluripotency factor" is used refer to the expression product of a gene whose function is associated with pluripotency, e.g., a polypeptide encoded by the gene. In some embodiments the pluripotency factor is one that is normally substantially not expressed in somatic cell types that constitute the body of an adult animal (with the exception of germ cells or precursors thereof). For example, the pluripotency factor may be one whose average level in ES cells is at least 50-fold or 100-fold greater than its average level in those terminally differentiated cell types present in the body of an adult mammal. In some embodiments, the pluripotency factor is one that is essential to maintain the viability or pluripotent state of ES cells in vivo and/or ES cells derived using conventional methods. Thus if the gene encoding the factor is knocked out or inhibited (i.e., its expression is eliminated or substantially reduced), the ES cells are not formed, die or, in some embodiments, differentiate. In some embodiments, inhibiting expression of a gene whose function is associated with pluripotency in an ES cell (resulting in, e.g., a reduction in the average steady state level of RNA transcript and/or protein encoded by the gene by at least 50%, 60%, 70%, 80%, 90%, 95%, or more) results in a cell that is viable but no longer pluripotent. In some embodiments the gene is characterized in that its expression in an ES cell decreases (resulting in, e.g., a reduction in the average steady state level of RNA transcript and/or protein encoded by the gene by at least 50%, 60%, 70%, 80%, 90%, 95%, or more) when the cell differentiates into a terminally differentiated cell.

A "pluripotency inducing gene", as used herein, refers to a gene whose expression, contributes to reprogramming somatic cells to a pluripotent state. "Pluripotency inducing factor" refers to an expression product of a pluripotency inducing gene. A pluripotency inducing factor may, but need not be, a pluripotency factor. Expression of an exogenously introduced pluripotency inducing factor may be transient, i.e., it may be needed during at least a portion of the reprogramming process in order to induce pluripotency and/or establish a stable pluripotent state but afterwards not required to maintain pluripotency. For example, the factor may induce expression of endogenous genes whose function is associated with pluripotency. These genes may then maintain the reprogrammed cells in a pluripotent state.

"Polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

"Polypeptide" refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

"Polypeptide variant" refers to any polypeptide differing from a naturally occurring polypeptide by amino acid insertion(s), deletion(s), and/or substitution(s). Variants may be naturally occurring or created using, e.g., recombinant DNA techniques or chemical synthesis. In some embodiments amino acid "substitutions" are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Insertions or deletions may range in size from about 1 to 20 amino acids, e.g., 1 to 10 amino acids. In some instances larger domains may be removed without substantially affecting function. In certain embodiments of the invention the sequence of a variant can be obtained by making no more than a total of 5, 10, 15, or 20 amino acid additions, deletions, or substitutions to the sequence of a naturally occurring enzyme. In some embodiments not more than 1%, 5%, 10%, or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

"Purified" or "substantially purified" as used herein denote that the indicated nucleic acid or polypeptide is present in the substantial absence of other biological macromolecules, e.g., polynucleotides, proteins, and the like. In one embodiment, the polynucleotide or polypeptide is purified such that it constitutes at least 90% by weight, e.g., at least 95% by weight, e.g., at least 99% by weight, of the polynucleotide(s) or polypeptide(s) present (but water, buffers, ions, and other small molecules, especially molecules having a molecular weight of less than 1000 daltons, can be present).

"RNA interference" is used herein consistently with its meaning in the art to refer to a phenomenon whereby double-stranded RNA (dsRNA) triggers the sequence-specific degradation or translational repression of a corresponding mRNA having complementarity to a strand of the dsRNA. It will be appreciated that the complementarity between the strand of the dsRNA and the mRNA need not be 100% but need only be sufficient to mediate inhibition of gene expression (also referred to as "silencing" or "knockdown"). For example, the degree of complementarity is such that the strand can either (i) guide cleavage of the mRNA in the RNA-induced silencing complex (RISC); or (ii) cause translational repression of the mRNA. In certain embodiments the double-stranded portion of the RNA is less than about 30 nucleotides in length, e.g., between 17 and 29 nucleotides in length. In mammalian cells, RNAi may be achieved by introducing an appropriate double-stranded nucleic acid into the cells or expressing a nucleic acid in cells that is then processed intracellularly to yield dsRNA therein. Nucleic acids capable of mediating RNAi are referred to herein as "RNAi agents". Exemplary nucleic acids capable of mediating RNAi are a short hairpin RNA (shRNA), a short interfering RNA (siRNA), and a microRNA precursor. These terms are well known and are used herein consistently with their meaning in the art. siRNAs typically comprise two separate nucleic acid strands that are hybridized to each other to form a duplex. They can be synthesized in vitro, e.g., using standard nucleic acid synthesis techniques. They can comprise a wide variety of modified nucleosides, nucleoside analogs and can comprise chemically or biologically modified bases, modified backbones, etc. Any modification recognized in the art as being useful for RNAi can be used. Some modifications result in increased stability, cell uptake, potency, etc. In certain embodiments the siRNA comprises a duplex about 19 nucleotides in length and one or two 3' overhangs of 1-5 nucleotides in length, which may be composed of deoxyribonucleotides. shRNA comprise a single nucleic acid strand that contains two complementary portions separated by a predominantly non-selfcomplementary region. The complementary portions hybridize to form a duplex structure and the non-selfcomplementary region forms a loop connecting the 3' end of one strand of the duplex and the 5' end of the other strand. shRNAs undergo intracellular processing to generate siRNAs.

MicroRNAs (miRNAs) are small, non-coding, single-stranded RNAs of about 21-25 nucleotides (in mammalian systems) that inhibit gene expression in a sequence-specific manner. They are generated intracellularly from precursors having a characteristic secondary structure comprised of a short hairpin (about 70 nucleotides in length) containing a duplex that often includes one or more regions of imperfect complementarity. Naturally occurring miRNAs are only partially complementary to their target mRNA and typically act via translational repression. RNAi agents modelled on endogenous microRNA precursors are of use in the invention. In some embodiments, a sequence encoding the stem portion of a stem-loop structure or encoding a complete stem-loop can be inserted into a nucleic acid comprising at least a portion of an endogenous microRNA primary transcript, e.g., in place of the sequence that encodes the endogenous microRNA or minimum (~70 nucleotide) microRNA hairpin.

"Reprogramming factor" refers to a gene, RNA, or protein that promotes or contributes to cell reprogramming, e.g., in vitro. In aspects of the invention relating to reprogramming factor(s), the invention provides embodiments in which the reprogramming factor(s) are of interest for reprogramming somatic cells to pluripotency in vitro. Examples of reprogramming factors of interest for reprogramming somatic cells to pluripotency in vitro are Oct4, Nanog, Sox2, Lin28, Klf4, c-Myc, and any gene/protein that can substitute for one or more of these in a method of reprogramming somatic cells in vitro. "Reprogramming to a pluripotent state in vitro", or "reprogramming to pluripotency in vitro", is used herein to refer to in vitro reprogramming methods that do not require and typically do not include nuclear or cytoplasmic transfer or cell fusion, e.g., with oocytes, embryos, germ cells, or pluripotent cells. Any embodiment or claim of the invention may specifically exclude compositions or methods relating to or involving nuclear or cytoplasmic transfer or cell fusion, e.g., with oocytes, embryos, germ cells, or pluripotent cells.

"Selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla luciferase*) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

The term "Wnt", or "Wnt protein" as used herein refers to a polypeptide having a naturally occurring amino acid sequence of a Wnt protein or a fragment, variant, or derivative thereof that at least in part retains the ability of the naturally occurring protein to bind to Wnt receptor(s) and activate Wnt signaling. In addition to naturally-occurring allelic variants of the Wnt sequences that may exist in the population, it will be appreciated that, as is the case for virtually all proteins, a variety of changes can be introduced into the sequences listed under the accession numbers in Table 1 (referred to as "wild type" sequences) without substantially altering the functional (biological) activity of the polypeptides. Such variants are included within the scope of the terms "Wnt", "Wnt protein", etc.

The variant could be, e.g., a polypeptide at least 80%, 85%, 90%, 95%, 98%, or 99% identical to full length Wnt. The variant could be a fragment of fully length Wnt. The variant could be a naturally occurring splice variant. The variant could be a polypeptide at least 80%, 85%, 90%, 95%, 98%, or 99% identical to a fragment of Wnt, wherein the fragment is at least 50%, 60%, 70%, 80%, 85%, 90%, 95%, 98%, or 99% as long as the full length wild type polypeptide or a domain thereof having an activity of interest such as the ability to bind to a Wnt receptor. In some embodiments the domain is at least 100, 200, 300, or 400 amino acids in length, beginning at any amino acid position in the sequence and extending toward the C-terminus. Variations known in the art to eliminate or substantially reduce the activity of the Wnt protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature Wnt polypeptide, by which is meant a Wnt polypeptide that has had one or more portions such as a signal peptide removed during normal intracellular proteolytic processing (e.g., during co-translational or post-translational processing). In some embodiments wherein the Wnt protein is produced other than by purifying it from cells that naturally express it, the protein is a chimeric polypeptide, by which is meant that it contains portions from two or more different species. In some embodiments wherein the Wnt protein is produced other than by purifying it from cells that naturally express it, the protein is a Wnt derivative, by which is meant that the protein comprises additional sequences not related to Wnt so long as those sequences do not substantially reduce the biological activity of the protein.

One of skill in the art will be aware of, or will readily be able to ascertain, whether a particular Wnt variant, fragment, or derivative is functional using assays known in the art. For example, the ability of a variant of a Wnt polypeptide to bind to a Wnt receptor can be assessed using standard protein binding assays. Convenient assays include measuring the ability to activate transcription of a reporter construct containing a TCF binding site operably linked to a nucleic acid sequence encoding a detectable marker such as luciferase. One assay involves determining whether the Wnt variant induces phosphorylation of β-catenin. Phosphorylation status can be determined using any suitable method, e.g., immunoblotting. Other assays involve testing the variant or fragment for known biological activities of Wnt. See, e.g., Barker, N. and Clevers, H., Nat Rev Drug Discov. 5(12):997-1014, 2006, which describes assays suitable for identifying agents that modulate Wnt pathway activity. Such assays may readily be adapted to identify or confirm activity of agents that activate Wnt pathway activity. In certain embodiments of the invention a functional variant or fragment has at least 50%, 60%, 70%, 80%, 90%, 95% or more of the activity of the full length wild type polypeptide.

"Wnt pathway activity" or "Wnt signaling" refers to the series of biochemical events that ensues following binding of a stimulatory ligand (e.g., a Wnt protein) to a receptor for a Wnt family member, ultimately leading to changes in gene transcription and, if in vivo, often leading to a characteristic biological effect in an organism.

Reprogramming Somatic Cells by Activating the Wnt Pathway

The present invention provides the recognition that activating the Wnt pathway is of use to reprogram somatic cells. The invention provides the additional recognition that activating the Wnt pathway increases the efficiency of reprogramming of somatic cells, e.g., when such cells are subjected to a treatment that would result in reprogramming of at least some cells. "Increase the efficiency of reprogramming" means to cause an increase in the percentage of cells that undergo reprogramming when a population of cells is subjected to a reprogramming treatment, typically resulting in a greater number of individual colonies of reprogrammed cells after a given time period. In some embodiments of the invention, activating the Wnt pathway according to the invention increases the number of reprogrammed cells and/or the number of colonies of reprogrammed cells and/or the percentage of cells that undergo reprogramming. The invention further provides the recognition that activating the Wnt pathway enables reprogramming of somatic cells that have not been genetically modified to increase their expression of an oncogene such as c-Myc. The invention thus provides ways to substitute for engineered expression of c-Myc in any method of reprogramming somatic cells that would otherwise involve engineering cells to express c-Myc. In some embodiments of the invention, activating the Wnt pathway is sufficient to allow reprogramming under conditions in which reprogramming would not otherwise occur.

The invention provides methods for generating reprogrammed somatic cells comprising modulating, e.g., increasing, activity of the Wnt pathway. The invention further provides compositions of use in the methods. In one aspect, the invention provides a method of reprogramming a somatic cell comprising modulating, e.g., increasing Wnt pathway activity in the cell. The invention further provides improved methods for reprogramming of somatic cells, the method comprising subjecting somatic cells to a treatment that may reprogram at least some of the cells, wherein the improvement comprises increasing the activity of a Wnt pathway in said cells. The treatment may be any treatment known in the art to be of use to reprogram somatic cells or considered to be of potential use for this purpose. In certain embodiments of the invention Wnt pathway activity is increased using activators of the Wnt pathway such as small molecules, soluble Wnt proteins, or agents that mediate RNA interference and thereby inhibit endogenous inhibitors of the Wnt pathway. In certain embodiments somatic cells to be reprogrammed are cultured in Wnt conditioned medium. In any of the embodiments of the invention, unless otherwise indicated or evident from the context, "reprogramming" can refer to reprogramming to a pluripotent state.

Wnts are a family of secreted proteins important for a wide array of developmental and physiological processes (Mikels, A J and Nusse, R., Oncogene, 25: 7461-7468, 2006). Wnts are related to one another in sequence and strongly conserved in structure and function across multiple species. Thus a Wnt protein displaying activity in one species may be used in other species to activate the Wnt pathway in such species and may be expected to display similar activity. Wnt family members include Wnt1, Wnt2, Wnt2b (also called Wnt13), Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16. Sequences of Wnt genes and proteins are known in the art. One of skill in the art can readily find the Gene ID, accession numbers, and sequence information for Wnt family members and other genes and proteins of interest herein in publicly available databases (see Table 1 for examples).

TABLE 1

Wnt pathway proteins, effectors, and regulators

| Gene | Gene ID | Accession numbers (mRNA/protein) |
|---|---|---|
| Wnt3a (mouse) | 22416 | NM_009522/NP_033548 |
| Wnt3a (human) | 89780 | NM_033131/NP_149122 |
| β-catenin (mouse) | 12387 | NM_007614/NP_031640 |
| β-catenin (human) | 1499 | NM_001098209/NP_001091679 |
| | | NM_001098210/NP_001091680 |
| | | NM_001904/NP_001895 |
| GSK3α (mouse) | 606496 | NM_001031667/NP_001026837 |
| GSK3α (human) | 2931 | NM_019884/NP_063937 |
| GSK3β (mouse) | 56637 | NM_019827/NP_062801 |
| GSK3β (human) | 605004 | NM_002093/NP_002084 |
| Sox2 (mouse) | 20674 | NM_011443/NP_035573 |
| Sox2 (human) | 6657 | NM_003106/NP_003097 |
| Klf4 (mouse) | 16600 | NM_010637/NP_034767 |
| Klf4 (human) | 9314 | NM_004235/NP_004226 |
| Oct4 (mouse) | 18999 | NM_013633/NP_038661 |
| Oct4 (human) | 5460 | NM_203289/NP_976034 |
| Oct4 (human) | 5460 | NM_002701/NP_002692 |
| Nanog (mouse) | 71950 | NM_028016.2/NP_082292.1 |
| Nanog (human) | 79923 | NM_024865/NP_079141 |
| Lin28 (mouse) | 83557 | NM_145833/NP_665832 |
| Lin28 (human) | 79727 | NM_024674/NP_078950 |

Wnt signaling is initiated by interaction of Wnt proteins with a variety of receptors, including members of the Frizzled (Fz) family of transmembrane receptors and members of the low-density-lipoprotein receptor-related protein (LRP) family (e.g., LRP5/LRP6). The extracellular Wnt signal stimulates intracellular signal transduction cascades including the canonical pathway, which regulates gene expression in the nucleus (reviewed by Logan C Y and Nusse, R. Annu. Rev. Cell Dev. Biol., 20:781-810, 2004) and several non-canonical pathways (reviewed by Kohn, A D and Moon, R T, Cell Calcium, 38: 439-446, 2005). Briefly, Wnt signaling via the canonical pathway leads to stabilization and nuclear localization of β-catenin, which assembles with members of the T-cell factor/lymphoid enhancer factor (TCF/LEF) family of transcription factors to form complexes that generally activate transcription. In the absence of Wnt signaling β-catenin is instead targeted for degradation by the β-catenin destruction complex, and TCF/LEFs form complexes that generally repress transcription. In the absence of Wnt signaling, kinases such as glycogen synthase kinase-3 (GSK3) and casein kinase 1 (CK1) phosphorylate β-catenin, which as a consequence is ubiquinated and targeted for destruction by the proteasome. Activation of the Wnt pathway thus results in diminished phosphorylation of β-catenin, thereby leading to its stabilization. Several endogenous proteins have been identified as inhibitors of Wnt signaling, including Dickkopf (Dkk), breakpoint cluster region protein (Bcr), proteins comprising a WIF (Wnt inhibitory factor) domain etc.

In certain embodiments of the invention the reprogramming methods comprise contacting a cell with an agent that modulates, e.g., increases, the activity of a Wnt pathway. In some embodiments, increasing the Wnt pathway induces the cell to become pluripotent and possess features characteristic of ES cells. The methods are thus of use to generate pluripotent, ES-like cells (iPS cells). In certain embodiments of the invention a treatment that causes increased activity of a Wnt pathway is one that results in increased intracellular levels of β-catenin. In certain embodiments of the invention, a treatment that causes increased activity of a Wnt pathway is one that results in increased nuclear translocation of β-catenin. In certain embodiments of the invention, a treatment that causes increased activity of a Wnt pathway is one capable of causing changes in gene expression characteristic of cells exposed to a source of biologically active Wnt protein. In some embodiments of the invention, reprogramming is modulated using a Wnt pathway inhibitor.

A considerable advance towards the goal of reprogramming somatic cells to a pluripotent state in vitro was achieved when it was shown that cell lines with some of the properties of ES cells could be produced by introducing genes encoding four transcription factors associated with pluripotency, i.e., Oct3/4, Sox2, c-Myc and Klf4, into mouse skin fibroblasts via retroviral infection, and then selecting cells that expressed a marker of pluripotency, Fbx15, in response to these factors (Takahashi, K. & Yamanaka, S. Cell 126, 663-676, 2006). However, the resulting cells differed from ES cells in their gene expression and DNA methylation patterns and when injected into normal mouse blastocysts did not result in live chimeras (animals carrying cells throughout their bodies from both the original blastocyst and from the introduced cells). Subsequent work improved on these results by performing more rigorous selection, resulting in derivation of stable reprogrammed cell lines that, based on reported transcriptional, imprinting (expression of alleles predetermined by the parent from which they originated) and chromatin-modification profiles, appeared essentially identical to ES cells (Okita, K., et al., 448, 313-317, 2007; Wernig, M. et al. Nature 448, 318-324, 2007; Maherali, N. et al. Cell Stem Cell 1, 55-70, 2007). Somatic cells that have been reprogrammed to a pluripotent state in vitro using these methods or other methods (e.g., involving application of small molecules) are referred to herein consistently with usage in the art as "induced pluripotent stem" (iPS) cells. Subsequently, it was shown that human somatic cells can also be reprogrammed to pluripotency using these factors. Furthermore, it was demonstrated that the combination of Oct4, Nanog, Sox2, and Lin28 was also able to reprogram somatic cells to a pluripotent state in vitro (Yu J, Science, 318(5858):1917-20, 2007). However, generation of these cells also involved engineering the cells to express multiple transcription factors and employed retroviral transduction.

Applicants have now shown that an increased number of colonies comprised of ES-like cells developed when somatic cells genetically engineered to express Oct4, Sox2, Klf4, and c-Myc were cultured with Wnt3a conditioned medium than when the cells were cultured in medium conditioned by control cells or in standard cell culture medium conventionally used for the propagation of ES cells. Applicants further showed that colonies comprised of ES-like cells developed when somatic cells engineered to express Oct4, Sox2, and Klf4 but not modified to express c-Myc were cultured in Wnt3a conditioned medium, whereas colonies of ES-like cells did not form within the 20 day time period shown in FIG. 1 when such cells were cultured in unconditioned medium or medium conditioned by control cells. In both cases, the colonies displayed morphological features characteristic of ES cell colonies and expression of a detectable marker indicative of Oct4 expression. By all criteria tested, the cells appear to be pluripotent, ES-like cells (iPS cells). Furthermore, culturing the somatic cells in Wnt3a conditioned medium appeared to select for reprogrammed cells. The colonies formed in the presence of Wnt3a conditioned medium appeared more homogenous than those obtained in the absence of Wnt3a conditioned medium. The methods are thus of use to facilitate identification of reprogrammed cells, and optionally to facilitate separation of such cells from cells that have not become reprogrammed, without the need for chemical selection relying on an introduced genetic element such as a gene whose expression product confers drug resistance or fluorescence. The methods are thus of use to generate reprogrammed cells that do not carry genetic modifications for purposes of selection or detection of the reprogrammed cells. Furthermore, the methods are of use to increase the average percentage of reprogrammed cells in a colony comprising reprogrammed cells relative to the average percentage of cells that would be reprogrammed in the absence of an agent that increases Wnt pathway activity.

Applicants and others have noticed that some iPS-like cells can form without infecting the cells with c-Myc virus. However, this is a low-efficiency event and could be at least in part a result of insertional mutagenesis wherein a viral integration event directly activates c-Myc or c-Myc target gene(s). In Applicants' experiments, at very late time points, some colonies were seen on the plates that were overexpressing Klf4, Sox2 and Oct4 (without introducing c-Myc virus), even without Wnt conditioned medium. Wnt-conditioned medium significantly reduced the time required and increased the efficiency of the reprogramming process. One aspect of the invention is that the faster timing of reprogramming achieved using the methods of the invention will facilitate the use of transient means of overexpression of pluripotency inducing factors for iPS formation (for example, transient transfection) and/or reprogramming by treating somatic cells with reprogramming agents such as proteins, small molecules, etc., instead of viral infection. In addition, Applicants propose that increased efficiency of iPS formation using the methods of the invention could be of particular use in reprogramming human cells, either with or without Myc overexpression.

Without limitation, the methods are thus of use to increase the speed of reprogramming somatic cells to iPS cells. Thus, the invention provides a method of increasing the speed of reprogramming somatic cells, comprising culturing a population of somatic mammalian cells in Wnt conditioned cell culture medium so that at least some of the cells are induced to become ES-like cells within a shorter period of time than would be the case in the absence of Wnt conditioned medium. The invention also provides a method of increasing the speed of reprogramming somatic cells comprising activating the Wnt pathway in a cultured population of somatic cells so that at least some of the cells are induced to become ES-like cells within a shorter period of time than would be the case if the Wnt pathway was not activated. The invention also provides a method of increasing the speed of reprogramming somatic cells comprising culturing a population of somatic mammalian cells in the presence of an agent that increases Wnt pathway activity so that at least some of the cells are induced to become ES-like cells within a shorter period of time than would be the case in the absence of said agent. In some embodiments of the invention, the period of time is 7 days, while in other embodiments the period of time is 10, 15, or 20 days. In some embodiments of the invention, the cells are treated (e.g., genetically engineered) so that they express Sox2, Klf4, Oct4, and c-Myc at levels greater than would be the case in the absence of such treatment. In some embodiments of the invention, the cells are treated so that they overexpress Sox2, Klf4, and Oct4 at levels greater than would be the case in the absence of such treatment, but are not genetically engineered to overexpress c-Myc. One method of treatment is infecting the cells with viruses (e.g., retrovirus, lentivirus) or transfecting the cells with viral vectors (e.g., retroviral, lentiviral) that contain the sequences of the factors operably linked to suitable expression control elements to drive expression in the cells following infection or transfection and, optionally integration into the genome as known in the art. Further details regarding the compositions and methods of the invention are provided below.

The invention provides a method of reprogramming a somatic cell, comprising culturing the cell in Wnt conditioned cell culture medium so that the cell becomes reprogrammed. In some embodiments, culturing the cell in Wnt conditioned cell culture medium induces the cell to become pluripotent and possess features characteristic of ES cells. The methods are thus of use to generate pluripotent, ES-like cells (iPS cells). In some embodiments, the Wnt conditioned cell culture medium comprises Wnt3a conditioned medium.

The term "conditioned medium" refers to a cell culture medium that has previously been used for culturing cells. A conditioned medium is characterized in that it contains soluble substances, e.g., signaling molecules, growth factors, hormones etc., which are produced by cells during their cultivation and released into the medium. As used herein, "Wnt conditioned medium" refers to conditioned medium that has been previously used for culturing cells that produce and secrete Wnt. The medium may be further described by reference to a particular Wnt protein produced by the cells. For example, "Wnt3a conditioned medium" refers to conditioned medium that has been previously used for culturing cells that produce Wnt3a. The cells may also produce other Wnts in addition to the particular Wnt specifically referred to. Any embodiment of the invention employing Wnt conditioned medium may employ Wnt3a conditioned medium unless otherwise indicated.

It will be appreciated that certain Wnts have similar biological activities to Wnt3a and/or are closely related in sequence to Wnt3a. Conditioned media prepared using cells that produce such Wnts are used in certain embodiments of the invention.

Conditioned medium may be prepared by methods known in the art. Such methods typically comprise culturing a first population of cells in a cell culture medium, and then harvesting the medium (typically without harvesting the cells). The harvested medium may be filtered to remove cell debris, etc. The conditioned medium (containing components secreted into the medium by the cells) may then be used to support the growth of a second population of cells. The cells are cultured in the medium for sufficient time to allow adequate concentration of released factors such as Wnt (and/or consumption of media components) to produce a medium that supports the reprogramming of somatic cells. In some embodiments, medium is conditioned by culturing for 24 h at 37° C. However, longer or shorter periods can be used such as between 24 and 72 hours. The cells can be used to condition multiple batches medium over additional culture periods, for as long as the cells retain their ability to condition the medium in an adequate fashion for the desired purpose.

The medium in which the cells are cultured to produce conditioned medium may be conventional cell culture medium capable of maintaining viability of the cells. In some embodiments, the medium is chemically defined. In some embodiments, the medium is similar or identical in composition to medium conventionally used to culture embryonic stem cells of the same species as the somatic cells to be reprogrammed using the conditioned medium. The base medium used for conditioning can have any of a number of different compositions, depending in part on the types of cells used. The medium must be able to support culture of the cell line used for the conditioning of the medium. In some embodiments, medium also supports culture of somatic cells prior to their being reprogrammed and, optionally, somatic cells that have been reprogrammed. However, the conditioned medium can be supplemented with other components, combined with other medium, etc., after conditioning so as to render it suitable for culturing somatic cells and reprogrammed somatic cells.

Suitable base media can be made from the following components: Dulbecco's modified Eagle's medium (DMEM), Invitrogen Cat. No. 11965-092; Knockout Dulbecco's modified Eagle's medium (KO DMEM), Invitrogen Cat. No. 10829-018; Ham's F12/50% DMEM basal medium; 200 mM L-glutamine, Invitrogen Cat. No. 15039-027; non-essential amino acid solution, Invitrogen Cat. No. 11140-050; beta-mercaptoethanol; human recombinant basic fibroblast growth factor (bFGF). Exemplary serum-containing ES medium is made with 80% DMEM (typically KO DMEM), 20% defined fetal bovine serum (FBS) not heat inactivated, 1% non-essential amino acids, 1 mM L-glutamine, and 0.1 mM β-mercaptoethanol. The medium is filtered and stored at 4° C. for no longer than 2 weeks. Serum-free ES medium may be prepared with 80% KO DMEM, 20% serum replacement, 1% non-essential amino acids, 1 mM L-glutamine, and 0.1 mM β-mercaptoethanol and a serum replacement such as Invitrogen Cat. No. 10828-028. The medium is filtered and stored at 4° C. Before combining with the cells used for conditioning, human bFGF can be added to a final concentration of 4 ng/mL. StemPro® hESC SFM (Invitrogen Cat. No. A1000701), a fully defined, serum- and feeder-free medium (SFM) specially formulated for the growth and expansion of human embryonic stem cells, is of use.

The cells used to prepare the conditioned medium may naturally produce Wnt. In some embodiments the cells used to prepare the medium are genetically engineered to increase their expression of Wnt, e.g., by transfecting them with a cDNA encoding Wnt, wherein the Wnt coding sequence is operably linked to expression control sequences active in the cells. See, e.g., Cai, L., et al., Cell Res. 17:62-72, 2007. In some embodiments, the cells produce and secrete Wnt into their medium resulting in medium having a concentration of between 100 ng/ml and 1000 ng/ml Wnt protein. In some embodiments, the cells produce and secrete Wnt into their medium resulting in medium having a concentration of between 200 ng/ml and 500 ng/ml Wnt protein. Cells that overexpress Wnt could also be used as feeder cells for purposes of reprogramming somatic cells.

Conditioned medium may be combined with unconditioned medium prior to use. For brevity, the resulting medium is still referred to as conditioned medium if it comprises at least 5% conditioned medium by volume. In some embodiments the amount (by volume) of conditioned medium is at least 10%, e.g., at least 10%, 20%, 30%, 40%, 50%, 60%, 70%, 80%, 90% or more conditioned medium. In some embodiments, the amount of conditioned medium is between about 50% and 75% by volume. The unconditioned medium may be standard cell culture medium. In some embodiments the unconditioned medium is medium conventionally used for propagating ES cells of the same species as the somatic cells to be reprogrammed.

The conditioned medium may be used immediately after being harvested from the cells used to produce it or may be stored (e.g., at about 4° C. or frozen) prior to use. The medium may be stored under conditions and for a time period consistent with maintaining the ability of the conditioned medium to support reprogramming in the methods of the invention. Without limitation, such conditions and time may be consistent with maintaining at least 20% of the original biological activity of secreted Wnt present in the medium, which may be assessed using methods mentioned above. The conditioned medium may be concentrated or otherwise processed, e.g., using standard methods, provided such concentration or processing is consistent with maintaining the ability of the concentrate to support reprogramming when added to unconditioned medium. Without limitation, such concentration or processing may be consistent with maintaining at least 20% of the original biological activity of secreted Wnt present in the medium. As noted in the Examples, Applicants' results suggest that normal fibroblasts (not engineered to overexpress Wnt) may secrete factors, perhaps including Wnt3a, that promote reprogramming, raising the possibility that somatic cells undergoing reprogramming in vitro, e.g., cells in culture that have been treated with retrovirus or otherwise engineered to express Oct4, Sox2, Klf4, and optionally c-Myc, may secrete such factors and thus contribute to their own reprogramming. In certain embodiments of the present invention, Wnt-conditioned medium has a greater concentration of Wnt protein and/or Wnt pathway activating activity than would be the case when unmodified somatic cells, e.g., fibroblasts, undergoing reprogramming are cultured in medium known in the art to be useful for culturing somatic cells undergoing reprogramming. In some embodiments, such concentration and/or Wnt pathway activating ability may be at least 1.5, 2, 5, 10, 20, or more times as great as present in medium in which control fibroblasts are cultured as described in Example 5.

Certain methods of the invention involve contacting a somatic cell in vitro with one or more defined agent(s) that modulate, e.g., increase, Wnt pathway activity. The cells may be maintained in standard cell culture medium known in the art. The agent(s) may be added to the medium prior to using it to culture the cells or during cell culture. The term "defined agent" in this context means that the structure, sequence, or identity of the agent that modulates, e.g., increases, Wnt pathway activity is known and/or the agent is chemically synthesized and/or the agent is (prior to addition to the medium) isolated or at least partially purified. For example, the agent may not be an uncharacterized or unidentified component of conditioned medium, cell or tissue lysate or extract, cell cytoplasm or nuclear material, etc.

A variety of agents may be used to increase Wnt pathway activity. Such agents are referred to herein as "Wnt pathway activators" or "Wnt agonists". The Wnt pathway activator may act directly by interacting with a Wnt receptor or indirectly by interacting with one or more intracellular components of the Wnt signaling pathway such as β-catenin, a kinase or phosphatase that acts on β-catenin, a transcription factor that assembles with β-catenin, etc. The activator may increase expression of Wnt or a Wnt pathway component such as β-catenin. In certain embodiments the Wnt pathway activator increases activity of the Wnt pathway to levels sufficient to enhance reprogramming of somatic cells. In certain embodiments of the invention the Wnt pathway activator inhibits degradation of β-catenin, thereby enhancing reprogramming of somatic cells. In certain embodiments of the invention, it is of interest to inhibit the Wnt pathway in somatic cells or in reprogrammed somatic cells. For example, Wnt pathway inhibitors can be used to characterize or explore the mechanism by which reprogramming occurs and/or to identify reprogramming agents (e.g., agents that do not act via the Wnt pathway). Furthermore, in certain embodiments of the invention, Wnt pathway inhibitors (e.g, small molecules, siRNA, proteins, etc.) may be of use to facilitate differentiation of reprogrammed, pluripotent cells to a desired cell type, e.g., in in vitro differentiation protocols.

In certain embodiments of the invention, the Wnt pathway activator or inhibitor is a protein or small molecule that binds to a Wnt receptor. For example, the Wnt pathway activator can be a soluble, biologically active Wnt protein.

In some embodiments the concentration of Wnt protein added to the medium is between 10 and 10,000 ng/ml, e.g., between 100 and 5,000 ng/ml, e.g., between 1,000 and 2,500 ng/ml or between 2,500 and 5,000 ng/ml, or between 5,000 and 10,000 ng/ml.

As noted above certain Wnts have similar biological activities to Wnt3a and/or are closely related in sequence to Wnt3a. Such Wnts and/or agents that mimic the activity of such Wnts are used in certain embodiments of the invention.

The Wnt protein may be isolated from naturally occurring sources (e.g., mammalian cells that naturally produce the protein), produced in eukaryotic or prokaryotic cells using recombinant expression technology, or chemically synthesized. Soluble, biologically active Wnt proteins may be prepared in purified form using methods known in the art. See, e.g., U.S. Pat. Pub. No. 20040248803 and Willert, K., et al., Nature, 423: 448-52, 2003. In certain embodiments the soluble, biologically active Wnt protein is Wnt3a. In certain embodiments the Wnt protein is co- or post-translationally modified as occurs when the Wnt protein is produced in a host cell that naturally expresses the Wnt protein. In other embodiments the Wnt protein is not co- or post-translationally modified as in nature. In certain embodiments the soluble, biologically active Wnt protein is modified with a lipid moiety such as palmitate. The lipid moiety may be attached to a conserved cysteine. For example, in certain embodiments the Wnt protein is palmitoylated on a conserved cysteine as known in the art. In certain embodiments the Wnt protein is glycosylated as occurs when the Wnt protein is produced in a mammalian host cell that naturally expresses the Wnt protein. In other embodiments the Wnt protein is not glycosylated as found in nature. Recombinant mouse Wnt3a is commercially available (e.g., from Millipore cat. no. GF145 or R&D Systems cat. no. 1324-WN-002).

In certain embodiments of the invention the Wnt pathway activator is an agent that increases the level of β-catenin, promotes its nuclear localization, or otherwise activates β-catenin signaling.

In certain embodiments of the invention the Wnt pathway activator is a small molecule, by which is meant an organic compound having multiple carbon-carbon bonds and a molecular weight of less than 1500 daltons. Typically such compounds comprise one or more functional groups that mediate structural interactions with proteins, e.g., hydrogen bonding, and typically include at least an amine, carbonyl, hydroxyl or carboxyl group, and in some embodiments at least two of the functional chemical groups. The small molecule agents may comprise cyclic carbon or heterocyclic structures and/or aromatic or polyaromatic structures substituted with one or more chemical functional groups and/or heteroatoms.

In certain embodiments of the invention the Wnt pathway activator is an agent that inhibits glycogen synthase kinase 3 (GSK3). These agents effectively "turn on" the Wnt pathway without the need for extracellular Wnt. GSK3 is a serine/threonine kinase, originally identified as a regulator of glucose metabolism (reviewed in Frame and Cohen, Biochem J 359:1-16, 2001; see also Cohen, Biochem Soc Trans 7:459-80, 1979; Embi et al., Eur J Biochem 107:519-27, 1980). "GSK3" as used herein refers to either or both isoforms of GSK3 (GSK3α and GSK3β). Inhibitors that inhibit either or both of these isoforms are of use. In certain embodiments the GSK3 inhibitor specifically inhibits GSK3 and does not substantially inhibit the majority of other mammalian kinases. In some embodiments the GSK3 inhibitor does not substantially inhibit at least 10 diverse mammalian kinases. In some embodiments the GSK3 inhibitor specifically inhibits both GSK3β and GSK3α. In some embodiments the GSK3 inhibitor specifically inhibits GSK3β but not GSK3α. For example, the IC50 for GSK3a may be at least 10-fold as great as for GSK3β. In some embodiments the GSK3 inhibitor specifically inhibits GSK3a but not GSK3β. For example, the IC50 for GSK3β may be at least 10-fold as great as for GSK3α. In certain embodiments the IC50 of the GSK3 inhibitor for GSK3 is at least 10-fold lower than its IC50 for the majority of other mammalian kinases. In certain embodiments the IC50 of the GSK3 inhibitor for GSK3 is less than 10 μM. In certain embodiments the IC50 of the GSK3 inhibitor for GSK3 is less than 1 μM. It will be understood that the GSK3 inhibitor should be capable of entering cells in sufficient quantities under the conditions used so as to inhibit GSK3 therein. In some embodiments the concentration of GSK3 inhibitor used is at least equal to the IC50 of the compound as measured in vitro. In some embodiments the concentration of GSK3 inhibitor used is no more than 100 times the IC50 of the compound as measured in vitro. In some embodiments the concentration used ranges between 0.5 and 50-fold the IC50 of the agent as measured in vitro.

Many potent and selective small molecule inhibitors of GSK3 have now been identified (Wagman A S, Johnson K W, Bussiere D E, Curr Pharm Des., 10(10):1105-37, 2004). Exemplary GSK3 inhibitors of use include the following: (1) BIO: (2'Z,3'E)-6-Bromoindirubin-3'-oxime. 6-bromoindirubin-3'-oxime (BIO) is a potent, reversible and ATP-competitive GSK-3 inhibitor (Polychronopoulos, P. et al. J. Med. Chem. 47, 935-946, 2004). (2) AR-A014418: N-(4-Methoxybenzyl)-N'-(5-nitro-1,3-thiazol-2-yl)urea. AR-A014418, inhibits GSK3 (IC50=104 nM), in an ATP-competitive manner (Ki=38 nM). AR-A014418 does not significantly inhibit cdk2 or cdk5 (IC50>100 μM) or 26 other kinases, demonstrating high specificity for GSK3 (Bhat, R., et al., J. Biol. Chem. 278, 45937-45945, 2003). (3) SB 216763: 3-(2,4-Dichlorophenyl)-4-(1-methyl-1H-indol-3-yl)-1H-pyrrole-2,5-dione. See, e.g., Smith, D. G., et al, Bioorg. Med. Chem. Lett. 11, 635-639, (2001) and Cross, D. A., et al., J. Neurochem. 77, 94-102, (2001), (4) SB 415286: 3-[(3-Chloro-4-hydroxyphenyl)amino]-4-(2-nitrophenyl)-1H-pyrrol-2,5-dione. SB 415286 is described in Smith, D. G., et al, Bioorg. Med. Chem. Lett. 11, 635-639, 2001 and Coughlan, M. P., et al, Chem. Biol. 10, 793-803, 2000, (5) TDZD-8: 4-Benzyl-2-methyl-1,2,4-thiadiazolidine-3,5-dione. This compound is a selective inhibitor of GSK-3, a thiadiazolidinone derivative, a non-ATP competitive inhibitor of GSK-3β (IC50=2 μM). It does not inhibit Cdk-1/cyclin B, CK-II, PKA or PKC at >100 μM. It has been proposed to bind to the kinase site of GSK-3β. (Martinez et al., J. Med. Chem. 45, 1292-1299, 2002); CHIR-911 and CHIR-837 (also referred to as CT-99021 and CT-98023 respectively). Chiron Corporation (Emeryville, Calif.) and related compounds are of use. Lithium chloride, sodium valproate, and GSK3 inhibitor II (Calbiochem) are other GSK3 inhibitors of use. Additional GSK3 inhibitors are described in U.S. Pat. Nos. 6,057,117 and 6,608,063; U.S. patent application publications 20040092535, 20040209878, 20050054663. Other GSK3 inhibitors of use are described in WO/2003/049739, which discloses PYRIMIDINE COMPOUNDS USEFUL AS GSK-3 INHIBITORS; WO/2002/085909, which discloses 9-DEAZAGUANINE DERIVATIVES AS INHIBITORS OF GSK-3, WO/2003/011287, which discloses PYRAZOLON DERIVATIVES AS INHIBITORS OF GSK-3, WO/2005/039485, and/or WO/2006/091737.

In certain embodiments of the invention the Wnt pathway activator is a casein kinase 1 (CK1) inhibitor. Examples include D4476, IC261, and CKI-7 (see, e.g., Rena, G., et al. EMBO reports 5(1), 60-65, 2004). Compounds that inhibit CK1 and GSK3 are disclosed in U.S. Pat. No. 7,098,204.

In certain embodiments of the invention the Wnt pathway activator is an activator of a phosphatase that naturally dephosphorylates β-catenin at one or more of the sites phosphorylated by GSK3 or CK1.

The CREB binding protein (CBP) and the closely related protein p300 can assemble with β-catenin and act as β-catenin binding transcriptional co-activators. For example, to generate a transcriptionally active complex, β-catenin recruits the transcriptional coactivators, CREB-binding protein (CBP) or its closely related homolog p300 (Hecht et al., EMBO J. 19:1839-50 (2000); Takemaru et al., J. Cell Biol. 149:249-54 (2000)) as well as other components of the basal transcription machinery. Other β-catenin co-activators include TBP, BRG1, BCL9/PYG, etc. The invention encompasses directly or indirectly modulating the interactions between β-catenin and any one or more of these co-activators so as to enhance the reprogramming of somatic cells. For example, the invention encompasses altering the relative participation of β-catenin in any one or more of these complexes relative to its participation in one or more other complexes. Agents such as small molecules may be used to selectively disrupt interaction of β-catenin with a particular co-activator, thereby potentially reducing transcription that would inhibit reprogramming or favor differentiation. Selective disruption may shift the balance towards interaction with a different co-activator to form a complex that enhances reprogramming. The agent may act directly on the complex or indirectly, e.g., by causing post-translational modification such as phosphorylation of β-catenin or a co-activator. In one embodiment, the agent is a compound described in U.S. Patent Pub. No. 20070128669 or an analog or derivative thereof, or an agent having the same mechanism of action. β-catenin interacting protein (also known as ICAT or CTNNBIP1) binds β-catenin and inhibits interaction between β-catenin and TCF family members (Gottardi, et al., Am J Physiol Cell Physiol. 286(4):C747-56, 2004). The encoded protein is a negative regulator of the Wnt signaling pathway. The invention encompasses inhibiting ICAT (which term includes any transcript variants or family members that inhibit the interaction of β-catenin and TCF) in order to activate the Wnt pathway. In certain embodiments of the invention, the agent that activates a Wnt pathway does so by inhibiting expression or activity of an endogenous inhibitor or negative regulator of the Wnt pathway. In some embodiments, the agent inhibits expression by RNA interference (RNAi). In some embodiments, the agent inhibits expression or activity of GSK3, ICAT, CK1, or CTNNBIP1.

In some embodiments an inhibitor of use in the present invention is an RNAi agent. One of skill in the art will be able to identify an appropriate RNAi agent to inhibit expression of a gene of interest. See, e.g., Yu, J-Y., et al., Molecular Therapy, 7(2): 228-236, 2003. The RNAi agent may inhibit expression sufficiently to reduce the average steady state level of the RNA transcribed from the gene (e.g., mRNA) or its encoded protein by, e.g., by at least 50%, 60%, 70%, 80%, 90%, 95%, or more). The RNAi agent may contain a sequence between 17-29 nucleotides long, e.g., 19-23 nucleotides long that is 100% complementary to the mRNA or contains up to 1, 2, 3, 4, or 5 nucleotides, or up to about 10-30% nucleotides, that do not participate in Watson-Crick base pairs when aligned with the mRNA to achieve the maximum number of complementary base pairs. The RNAi agent may contain a duplex between 17-29 nucleotides long in which all nucleotides participate in Watson-Crick base pairs or in which up to about 10-30% of the nucleotides do not participate in a Watson-Crick base pair. One of skill in the art will be aware of which sequence characteristics are often associated with superior siRNA functionality and algorithms and rules by which such siRNAs can be designed (see, e.g., Jagla, B., et al, RNA, 11(6):864-72, 2005). The methods of the invention can, but need not, employ siRNAs having such characteristics. In some embodiments, the sequence of either or both strands of the RNAi agent is/are chosen to avoid silencing non-target genes, e.g., the strand(s) may have less than 70%, 80%, or 90% complementarity to any mRNA other than the target mRNA. In some embodiments, multiple different sequences are used. Table 1 lists the Gene IDs of the human and mouse genes encoding GSK3 and the nucleic acid (mRNA) and protein sequence accession numbers. RNAi agents capable of silencing mammalian genes are commercially available (e.g., from suppliers such as Qiagen, Dharmacon, Invitrogen, etc.). If multiple isoforms exist, one can design siRNAs or shRNAs targeted against a region present in all of the isoforms expressed in a given cell of interest.

Methods for silencing genes by transfecting cells with siRNA or constructs encoding shRNA are known in the art. To express an RNAi agent in somatic cells, a nucleic acid construct comprising a sequence that encodes the RNAi agent, operably linked to suitable expression control elements, e.g., a promoter, can be introduced into the cells as known in the art. For purposes of the present invention a nucleic acid construct that comprises a sequence that encodes an RNA or polypeptide of interest, the sequence being operably linked to expression control elements such as a promoter that direct transcription in a cell of interest, is referred to as an "expression cassette". The promoter can be an RNA polymerase I, II, or III promoter functional in somatic mammalian cells. In certain embodiments, expression of the RNAi agent is conditional. In some embodiments, expression is regulated by placing the sequence that encodes the RNAi agent under control of a regulatable (e.g., inducible or repressible) promoter.

Constitutively active versions of proteins such as β-catenin or other components of the Wnt signalling pathway are also of use. N-terminal truncation or deletion of the potential GSK-3 phosphorylation site in the N-terminal region or a missense mutation of the serine or threonine residues therein results in the accumulation of truncated or normal sized β-catenin and then in activation of β-catenin-mediated signal (de La Coste PNAS, 95(15): 8847-8851, 1998). Dominant negative versions of endogenous proteins that inhibit Wnt signalling are also of use. In some embodiments, somatic cells are engineered to express these proteins. In some embodiments, the protein is added to the culture medium.

In some embodiments, cells are treated to enhance uptake of a Wnt pathway activator that acts intracellularly. For example, the cell membrane may be partially permeabilized. In some embodiments, a Wnt pathway activator is modified to comprise an amino acid sequence that enhances cellular uptake of molecules by cells (also referred to as a "protein transduction domain"). Such uptake-enhancing amino acid sequences are found, e.g., in HIV-1 TAT protein, the herpes simplex virus 1 (HSV-1) DNA-binding protein VP22, the Drosophila Antennapedia (Antp) transcription factor, etc. Artificial sequences are also of use. See, e.g., Fischer et al, Bioconjugate Chem., Vol. 12, No. 6, 2001 and U.S. Pat. No. 6,835,810.

Without limitation, the invention contemplates use in the methods of the present invention of any of the compositions and approaches disclosed in U.S. Patent Pub. No. 20060147435 as being useful for promoting Wnt/β-catenin signaling.

In some embodiments of the invention, somatic cells are treated so that they express a Wnt protein at levels greater than would be the case without such treatment. In some embodiments, somatic cells are genetically engineered to stably or transiently express a Wnt protein at levels greater than would be the case without such treatment. In some embodiments of the invention somatic cells are treated so that they express a Wnt pathway component such as β-catenin or a TCF/LEF at levels greater than would be the case without such treatment. In some embodiments of the invention, somatic cells are genetically engineered to stably or transiently express a Wnt pathway component such as β-catenin or a TCF/LEF at levels greater than would be the case without such treatment.

Methods of the invention may include treating the cells with multiple reprogramming agents either concurrently (i.e., during time periods that overlap at least in part) or sequentially and/or repeating the steps of treating the cells with an agent. The agent used in the repeating treatment may be the same as, or different from, the one used during the first treatment. The cells may be contacted with a reprogramming agent for varying periods of time. In some embodiments, the cells are contacted with the agent for a period of time between 1 hour and 60 days, e.g., between 10 and 30 days, e.g., for about 15-20 days. Reprogramming agents may be added each time the cell culture medium is replaced. The reprogramming agent(s) may be removed prior to performing a selection to enrich for pluripotent cells or assessing the cells for pluripotency characteristics.

Reprogramming agents or candidate reprogramming agents of interest include a variety of compounds. Exemplary compounds include agents that inhibit histone deacetylation, e.g., histone deacetylase (HDAC) inhibitors and agents that inhibit DNA methylation, e.g., DNA methyltransferase inhibitors. Without wishing to be bound by theory, DNA demethylation can regulate gene expression by "opening" the chromatin structure detectable as increased nuclease sensitivity. This remodeling of chromatin structure allows transcription factors to bind to the promoter regions, assembly of the transcription complex, and gene expression.

The major classes of HDAC inhibitors include (a) Small chain fatty acids (e.g., valproic acid); (b) hydroxamate small molecule inhibitors (e.g., SAHA and PXD101); (c) Non-hydroxamate small molecule inhibitors, e.g., MS-275; and (d) Cyclic peptides: e.g., depsipeptide (see, e.g., Carey N and La Thangue N B, Curr Opin Pharmacol.; 6(4):369-75, 2006). Examples of histone deacetylase inhibitors include Trichostatin A: [R-(E,E)]-7-[4-(Dimethylamino)phenyl]-N-hydroxy-4,6-dimethyl-7-oxo-2,4-heptadienamide, which inhibits histone deacetylase at nanomolar concentrations; resultant histone hyper-acetylation leads to chromatin relaxation and modulation of gene expression. (Yoshida, M., et al., Bioessays 17, 423-430, 1995; Minucci, S., et al., Proc. Natl. Acad. Sci. USA 94, 11295-11300, 1997; Brehm, A., et al., 1998; Medina, V., et al., Induction of caspase-3 protease activity and apoptosis by butyrate and trichostatin A (inhibitors of histone deacetylase): dependence on protein synthesis and synergy with a mitochondrial/cytochrome c-dependent pathway. Cancer Res. 57, 3697-3707, 1997; Kim, M. S., et al., Inhibition of histone deacetylase increases cytotoxicity to anticancer drugs targeting DNA. Cancer Res. 63, 7291-7300, 2003); Apicidin: Cyclo[(2S)-2-amino-8-oxodecanoyl-1-methoxy-L-tryptophyl-L-isoleucyl-(2R)-2-piperidinexcarbonyl] (Kwon, S. H., et al. J. Biol. Chem. 18, 2073, 2002; Han, J. W., et al. Cancer Res. 60, 6068, 2000; Colletti, S. L., et al. Bioorg. Med. Chem. 11, 107, 2001; Kim, J. S., et al. Biochem. Biophys. Res. Commun. 281, 866, 2001).

A variety of DNA methylation inhibitors are known in the art and are of use in the invention. See, e.g., Lyko, F. and Brown, R., *JNCI Journal of the National Cancer Institute*, 97(20):1498-1506, 2005. Inhibitors of DNA methylation include nucleoside DNA methyltransferase inhibitors such as decitabine (2'-deoxy-5-azacytidine), 5-azadeoxycytidine, and zebularine, non-nucleoside inhibitors such as the polyphenol (−)-epigallocatechin-3-gallate (EGCG) and the small molecule RG108 (2-(1,3-dioxo-1,3-dihydro-2H-isoindol-2-yl)-3-(1H-indol-3-yl)propanoic acid), compounds described in WO2005085196 and phthalamides, succinimides and related compounds as described in WO2007007054. Three additional classes of compounds are: (1) 4-Aminobenzoic acid derivatives, such as the antiarrhythmic drug procainamide and the local anesthetic procaine; (2) the psammaplins, which also inhibits histone deacetylase (Pina, I. C., *J Org. Chem.*, 68(10):3866-73, 2003); and (3) oligonucleotides, including siRNAs, shRNAs, and specific antisense oligonucleotides, such as MG98. DNA methylation inhibitors may act by a variety of different mechanisms. The nucleoside inhibitors are metabolized by cellular pathways before being incorporated into DNA. After incorporation, they function as suicide substrates for DNMT enzymes. The nonnucleoside inhibitors procaine, epigallocatechin-3-gallate (EGCG), and RG108 have been proposed to inhibit DNA methyltransferases by masking DNMT target sequences (i.e., procaine) or by blocking the active site of the enzyme (i.e., EGCG and RG108). In some embodiments of the invention, combinations of DNA methylation inhibitors are used. In some embodiments, the concentrations are selected to minimize toxic effects on cells. In some embodiments agents that incorporate into DNA (or whose metabolic products incorporate into DNA) are not used.

DNA methyltransferase (DNMT1, 3a, and/or 3b) and/or one or more HDAC family members can alternatively or additionally be inhibited using RNAi agents.

The invention encompasses use of Wnt-conditioned medium, soluble Wnt or small molecules that modulate the Wnt signaling pathway in combination with other transient cues, e.g., small molecules, that can replace Oct4, Sox2, Klf4, Nanog, and/or Lin28 retroviruses in reprogramming somatic cells to pluripotency. The invention provides a composition comprising a Wnt pathway modulator and at least one compound selected from the group consisting of: HDAC inhibitors and DNA methylation inhibitors. The invention provides a composition comprising a Wnt pathway modulator, at least one HDAC inhibitor, and at least one DNA methylation inhibitor. The invention provides cell culture medium containing any of the above combinations of agents. In certain embodiments, the HDAC inhibitor is any HDAC inhibitor mentioned above. In certain embodiments, the DNA methylation inhibitor is any HDAC inhibitor mentioned above. In certain embodiments, the Wnt pathway modulator activates the Wnt pathway. In certain embodiments, the cell culture medium comprises Wnt-conditioned medium, e.g., Wnt3a-CM, as the source of Wnt pathway modulator. In certain embodiments, the Wnt pathway modulator is a small molecule. In certain embodiments, the composition comprises somatic cells. In certain embodiments, the somatic cells are engineered to express at least one of the transcription factors Oct4, Nanog, Sox2, Klf4, and Lin28.

Somatic Cells and Reprogrammed Somatic Cells

Somatic cells of use the invention may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. The cells may be maintained in cell culture following their isolation from a subject. In certain embodiments, the cells are passaged once or more following their isolation from the individual (e.g., between 2-5, 5-10, 10-20, 20-50, 50-100 times, or more) prior to their use in a method of the invention. They may be frozen and subsequently thawed prior to use. In some embodiments, the cells will have been passaged no more than 1, 2, 5, 10, 20, or 50 times following their isolation from the individual prior to their use in a method of the invention.

Somatic cells of use in the present invention include mammalian cells, such as, for example, human cells, non-human primate cells, or mouse cells. They may be obtained by well-known methods from various organs, e.g., skin, lung, pancreas, liver, stomach, intestine, heart, reproductive organs, bladder, kidney, urethra and other urinary organs, etc., generally from any organ or tissue containing live somatic cells. Mammalian somatic cells useful in various embodiments of the present invention include, for example, fibroblasts, adult stem cells, sertoli cells, granulosa cells, neurons, pancreatic islet cells, epidermal cells, epithelial cells, endothelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, cardiac muscle cells, skeletal muscle cells, etc., generally any living somatic cells.

Somatic cells may be treated so as to cause them to express or contain one or more reprogramming factor, pluripotency factor, and/or pluripotency inducing factor, at levels greater than would be the case in the absence of such treatment. For example, somatic cells may be genetically engineered to express one or more genes encoding one or more such factor(s) and/or may be treated with agent(s) that increase expression of one or more endogenous genes encoding such factors and/or stabilize such factor(s). The agent could be, for example, a small molecule, a nucleic acid, a polypeptide, etc. In some embodiments, factors such as pluripotency factors are introduced into somatic cells, e.g., by microinjection or by contacting the cells with the factors under conditions in which the factors are taken up by the cells. In some embodiments, the factors are modified to incorporate a protein transduction domain. In some embodiments, the cells are permeabilized or otherwise treated to increase their uptake of the factors. Exemplary factors are discussed below.

The transcription factor Oct4 (also called Pou5f1, Oct-3, Oct3/4) is an example of a pluripotency factor. Oct4 has been shown to be required for establishing and maintaining the undifferentiated phenotype of ES cells and plays a major role in determining early events in embryogenesis and cellular differentiation (Nichols et al., 1998, Cell 95:379-391; Niwa et al., 2000, Nature Genet. 24:372-376). Oct4 expression is down-regulated as stem cells differentiate into more specialized cells. Nanog is another example of a pluripotency factor. Nanog is a homeobox-containing transcription factor with an essential function in maintaining the pluripotent cells of the inner cell mass and in the derivation of ES cells from these. Furthermore, overexpression of Nanog is capable of maintaining the pluripotency and self-renewing characteristics of ESCs under what normally would be differentiation-inducing culture conditions. (See Chambers et al., 2003, Cell 113: 643-655; Mitsui et al., Cell. 2003, 113(5):631-42). Sox2, another pluripotency factor, is an HMG domain-containing transcription factor known to be essential for normal pluripotent cell development and maintenance (Avilion, A., et al., Genes Dev. 17, 126-140, 2003). Klf4 is a Krüppel-type zinc finger transcription factor initially identified as a Klf family member expressed in the gut (Shields, J. M, et al., J. Biol. Chem. 271:20009-20017, 1996). Overexpression of Klf4 in mouse ES cells was found to prevent differentiation in embryoid bodies formed in suspension culture, suggesting that Klf4 contributes to ES self renewal (Li, Y., et al., Blood 105:635-637, 2005). Sox2 is a member of the family of SOX (sex determining region Y-box) transcription factors and is important for maintaining ES cell self-renewal. c-Myc is a transcription factor that plays a myriad of roles in normal development and physiology as well as being an oncogene whose dysregulated expression or mutation is implicated in various types of cancer (reviewed in Pelengaris S, Khan M., Arch Biochem Biophys. 416(2):129-36, 2003; Cole M D, Nikiforov M A, Curr Top Microbiol Immunol., 302:33-50, 2006). In some embodiments, such factors are selected from: Oct4, Sox2, Klf4, and combinations thereof. In some embodiments, a different, functionally overlapping Klf family member such as Klf2 is substituted for Klf4. In some embodiments, the factors include at least Oct4. In some embodiments, the factors include at least Oct4 and a Klf family member, e.g., Klf2. Lin28 is a developmentally regulated RNA binding protein. In some embodiments, somatic cells are treated so that they express or contain one or more reprogramming factors selected from: Oct4, Sox2, Klf4, Nanog, Lin28, and combinations thereof. CCAAT/enhancer-binding-protein-alpha (C/EBPalpha) is another protein that promotes reprogramming at least in certain cell types, e.g., lymphoid cells such as B-lineage cells, is considered a reprogramming factor for such cell types, and is of use in certain embodiments of the invention, e.g., in combination with one or more of the pluripotency genes and/or Wnt pathway modulators described herein.

Other genes of interest are involved in chromatin remodeling and/or are have been shown to be important for maintaining pluripotency of ES cells. Optionally the gene is one that is downregulated as the cells differentiate and/or is not expressed in adult somatic cells. Other genes of interest encode microRNA precursors that have been associated with multipotency or pluripotency and/or that are naturally expressed in multipotent or pluripotent cells. Other genes of interest include encode RNAi agents that inhibit genes that are targets of endogenous microRNAs that are naturally expressed in multipotent or pluripotent cells.

In one embodiment, the exogenously introduced gene may be expressed from a chromosomal locus other than the chromosomal locus of an endogenous gene whose function is associated with pluripotency. Such a chromosomal locus may be a locus with open chromatin structure, and contain gene(s) whose expression is not required in somatic cells, e.g., the chromosomal locus contains gene(s) whose disruption will not cause cells to die. Exemplary chromosomal loci include, for example, the mouse ROSA 26 locus and type II collagen (Col2a1) locus (See Zambrowicz et al., 1997).

Methods for expressing genes in cells are known in the art. Generally, a sequence encoding a polypeptide or functional RNA such as an RNAi agent is operably linked to appropriate regulatory sequences. The term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express cDNAs.

The exogenously introduced gene may be expressed from an inducible or repressible regulatory sequence such that its expression can be regulated. The term "inducible regulatory sequence", as used herein, refers to a regulatory sequence that, in the absence of an inducer (such as a chemical and/or biological agent) or combination of inducers, does not direct expression, or directs low levels of expression of an operably linked nucleic acid sequence such as a cDNA, and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee et al. P.N.A.S. USA (1988), 85, 1204-1208; (1981), 294, 228-232; Klock et al. Nature (1987), 329, 734-736; Israel and Kaufman, Nucleic Acids Res. (1989), 17, 2589-2604), promoters that respond to chemical agents, such as glucose, lactose, galactose or antibiotic. A "repressible regulatory sequence" is one that directs expression of an operably linked nucleic acid sequence in the absence of a specific agent or combination of agents that inhibits expression.

A tetracycline-inducible promoter is an example of an inducible promoter that responds to an antibiotic. See Gossen, M. and Bujard, H., Annu Rev Genet. Vol. 36: 153-173 2002 and references therein. The tetracycline-inducible promoter comprises a minimal promoter linked operably to one or more tetracycline operator(s). The presence of tetracycline or one of its analogues leads to the binding of a transcription activator to the tetracycline operator sequences, which activates the minimal promoter and hence the transcription of the associated cDNA. Tetracycline analog includes any compound that displays structural similarity with tetracycline and is capable of activating a tetracycline-inducible promoter. Exemplary tetracycline analogs include, for example, doxycycline, chlorotetracycline and anhydrotetracycline.

In some embodiments of the invention, expression of an introduced gene, e.g., a gene encoding a reprogramming factor or RNAi agent is transient. Transient expression can be achieved by transient transfection or by expression from a regulatable promoter. In some embodiments, expression can be regulated by, or is dependent on, expression of a site-specific recombinase. Recombinase systems include the Cre-Lox and Flp-Frt systems, among others (Gossen, M. and Bujard, H., 2002). In some embodiments, a recombinase is used to turn on expression by removing a stopper sequence that would otherwise separate the coding sequence from expression control sequences. In some embodiments, a recombinase is used to excise at least a portion of a gene after pluripotency has been induced. In some embodiments, the recombinase is expressed transiently, e.g., it becomes undetectable after about 1-2 days, 2-7 days, 1-2 weeks, etc. In some embodiments the recombinase is introduced from external sources. Optionally the recombinase in these embodiments a protein transduction domain.

Reprogrammed somatic cells may be assessed for one or more pluripotency characteristic(s). The presence of pluripotency characteristic(s) indicates that the somatic cells have been reprogrammed to a pluripotent state. The term "pluripotency characteristics", as used herein, refers to characteristics associated with and indicative of pluripotency, including, for example, the ability to differentiate into cells derived from all three embryonic germ layers all types and a gene expression pattern distinct for a pluripotent cell, including expression of pluripotency factors and expression of other ES cell markers.

To assess potentially reprogrammed somatic cells for pluripotency characteristics, one may analyze such cells for particular growth characteristics and ES cell-like morphology. Cells may be injected subcutaneously into immunocompromised SCID mice to determine whether they induce teratomas (a standard assay for ES cells). ES-like cells can be differentiated into embryoid bodies (another ES specific feature). Moreover, ES-like cells can be differentiated in vitro by adding certain growth factors known to drive differentiation into specific cell types. Self-renewing capacity, marked by induction of telomerase activity, is another pluripotency characteristic that can be monitored. One may carry out functional assays of the reprogrammed somatic cells by introducing them into blastocysts and determining whether the cells are capable of giving rise to all cell types. See Hogan et al., 2003. If the reprogrammed cells are capable of forming a few cell types of the body, they are multipotent; if the reprogrammed cells are capable of forming all cell types of the body including germ cells, they are pluripotent.

One may also examine the expression of an individual pluripotency factor in the reprogrammed somatic cells to assess their pluripotency characteristics. Additionally or alternately, one may assess the expression of other ES cell markers. Stage-specific embryonic 1 5 antigens-1, -3, and -4 (SSEA-1, SSEA-3, SSEA-4) are glycoproteins specifically expressed in early embryonic development and are markers for ES cells (Solter and Knowles, 1978, Proc. Natl. Acad. Sci. USA 75:5565-5569; Kannagi et al., 1983, EMBO J. 2:2355-2361). Elevated expression of the enzyme alkaline phosphatase (AP) is another marker associated with undifferentiated embryonic stem cells (Wobus et al., 1 984, Exp. Cell 152:212-219; Pease et al., 1990, Dev. Biol. 141:322-352). Additional ES cell markers are described in Ginis, I., et al., *Dev. Biol.,* 269: 369-380, 2004 and in The International Stem Cell Initiative, Adewumi O, et al., Nat. Biotechnol., 25(7): 803-16, 2007 and references therein. For example, TRA-1-60, TRA-1-81, GCTM2 and GCT343, and the protein antigens CD9, Thy1 (also known as CD90), class 1 HLA, NANOG, TDGF1, DNMT3B, GABRB3 and GDF3, REX-1, TERT, UTF-1, TRF-1, TRF-2, connexin43, connexin45, Foxd3, FGFR-4, ABCG-2, and Glut-1 are of use.

One may perform expression profiling of the reprogrammed somatic cells to assess their pluripotency characteristics. Pluripotent cells, such as embryonic stem cells, and multipotent cells, such as adult stem cells, are known to have a distinct pattern of global gene expression. See, for example, Ramalho-Santos et al., Science 298: 597-600, 2002; Ivanova et al., Science 298: 601-604, 2002; Boyer, L A, et al. Nature 441, 349, 2006, and Bernstein, B E, et al., Cell 125 (2), 315, 2006. One may assess DNA methylation, gene expression, and/or epigenetic state of cellular DNA, and/or developmental potential of the cells, e.g., as described in Wernig, M., et al., Nature, 448:318-24, 2007. Cells that are able to form teratomas containing cells having characteristics of endoderm, mesoderm, and ectoderm when injected into SCID mice and/or possess ability to participate (following injection into murine blastocysts) in formation of chimeras that survive to term are considered pluripotent. Another method of use to assess pluripotency is determining whether the cells have reactivated a silent X chromosome.

Somatic cells may be reprogrammed to gain either a complete set of the pluripotency characteristics. Alternatively, somatic cells may be reprogrammed to gain only a subset of the pluripotency characteristics.

Certain methods of the invention include a step of selecting cells that express a marker that is expressed by multipotent or pluripotent cells. The marker may be specifically expressed in such cells. Standard cell separation methods, e.g., flow cytometry, affinity separation, etc. may be used. Alternately or additionally, one could select cells that do not express markers characteristic of somatic cells from which the potentially reprogrammed cells were derived and which are not expressed in ES cells generated using conventional methods. Other methods of separating cells may utilize differences in average cell size or density that may exist between pluripotent cells and somatic cells. For example, cells can be filtered through materials having pores that will allow only certain cells to pass through.

In some embodiments. the somatic cells contain a nucleic acid comprising regulatory sequences of a gene encoding a pluripotency factor operably linked to a selectable or detectable marker (e.g., GFP or neo). The nucleic acid sequence encoding the marker may be integrated at the endogenous locus of the gene encoding the pluripotency factor (e.g., Oct4) or the construct may comprise regulatory sequences operably linked to the marker. Expression of the marker may be used to select, identify, and/or quantify reprogrammed cells.

Any of the methods of the invention that relate to generating a reprogrammed somatic cell may include a step of obtaining a somatic cell or obtaining a population of somatic cells from an individual in need of cell therapy. Reprogrammed somatic cells are generated, selected, or identified from among the obtained cells or cells descended from the obtained cells. Optionally the cell(s) are expanded in culture prior to generating, selecting, or identifying reprogrammed somatic cell(s) genetically matched to the donor.

In some embodiments colonies are subcloned and/or passaged once or more in order to obtain a population of cells enriched for ES-like cells. The enriched population may contain at least 95%, 96%, 97%, 98%, 99% or more, e.g., 100% ES-like cells. The invention provides cell lines of somatic cells that have been stably and heritably reprogrammed to an ES-like state.

In some embodiments. the methods are practiced using somatic cells that are not genetically engineered for purposes of identifying or selecting reprogrammed cells. The resulting reprogrammed somatic cells do not contain exogenous genetic material that has been introduced into said cells (or ancestors of said cells) by the hand of man, e.g., for purposes of identifying or selecting reprogrammed cells. In some embodiments. the somatic cells and reprogrammed somatic cells derived therefrom do contain exogenous genetic material in their genome, but such genetic material is introduced for purposes of correcting a genetic defect in such cells or enabling such cells to synthesize a desired protein for therapeutic purposes and is not used to identify or select reprogrammed cells.

In some embodiments, the methods employ morphological criteria to identify reprogrammed somatic cells from among a population of somatic cells that are not reprogrammed. In some embodiments, the methods employ morphological criteria to identify somatic cells that have been reprogrammed to an ES-like state from among a population of cells that are not reprogrammed or are only partly reprogrammed to an ES-like state. "Morphological criteria" is used in a broad sense to refer to any visually detectable feature or characteristic of the cells or colonies. Morphological criteria include, e.g., the shape of the colonies, the sharpness of colony boundaries, the density, small size, and rounded shape of the cells relative to non-reprogrammed cells, etc. FIG. 1 shows colonies of cells displaying morphological criteria indicative of cells that have been reprogrammed to an ES-like state. Note the dense colonies composed of small, rounded cells, and the sharp colony boundaries. The invention encompasses identifying and, optionally, isolating colonies (or cells from colonies) wherein the colonies display one or more such characteristics. The reprogrammed somatic cells may be identified as colonies growing in a first cell culture dish (which term refers to any vessel, plate, dish, receptacle, container, etc., in which living cells can be maintained in vitro) and the colonies, or portions thereof, transferred to a second cell culture dish, thereby isolating reprogrammed somatic cells. The cells may then be further expanded.

Methods of Screening for an Agent that Reprograms or Contributes to Reprogramming Somatic Cells The present invention also provides methods for identifying an agent that, alone or in combination with one or more other agents, reprograms somatic cells to a less differentiated state. The invention further provides agents identified according to the methods. In one embodiment, the methods comprise contacting somatic cells with a Wnt pathway activator and a candidate agent and determining whether the presence of the candidate agent results in enhanced reprogramming (e.g., increased reprogramming speed and/or efficiency) relative to that which would occur if cells had not been contacted with the candidate agent. In some embodiments, the Wnt activator and candidate agent are present together in the cell culture medium while in other embodiments the Wnt activator and the candidate agent are not present together (e.g., the cells are exposed to the agents sequentially). The cells may be maintained in culture for, e.g., at least 3 days, at least 5 days, up to 10 days, up to 15 days, up to 30 days, etc., during which time they are contacted with the Wnt activator and the candidate agent for all or part of the time. In some embodiments, the agent is identified as an agent that reprograms cells if there are at least 2, 5, or 10 times as many reprogrammed cells or colonies comprising predominantly reprogrammed cells after said time period than if the cells have not been contacted with the agent.

A candidate agent can be any molecule or supramolecular complex, e.g. a polypeptide, peptide (which is used herein to refer to a polypeptide containing 60 amino acids or less), small organic or inorganic molecule (i.e., molecules having a molecular weight less than 1,500 Da, 1000 Da, or 500 Da), polysaccharide, polynucleotide, etc. which is to be tested for ability to reprogram cells In some embodiments, the candidate agents are organic molecules, particularly small organic molecules, comprising functional groups that mediate structural interactions with proteins, e.g., hydrogen bonding, and typically include at least an amine, carbonyl, hydroxyl or carboxyl group, and in some embodiments at least two of the functional chemical groups. The candidate agents may comprise cyclic carbon or heterocyclic structures and/or aromatic or polyaromatic structures substituted with one or more chemical functional groups and/or heteroatoms.

Candidate agents are obtained from a wide variety of sources, as will be appreciated by those in the art, including libraries of synthetic or natural compounds. In some embodiments, candidate agents are synthetic compounds. Numerous techniques are available for the random and directed synthesis of a wide variety of organic compounds and biomolecules. In some embodiments, the candidate modulators are provided as mixtures of natural compounds in the form of bacterial, fungal, plant and animal extracts, fermentation broths, conditioned media, etc., that are available or readily produced.

In some embodiments, a library of compounds is screened. A library is typically a collection of compounds that can be presented or displayed such that the compounds can be identified in a screening assay. In some embodiments, compounds in the library are housed in individual wells (e.g., of microtiter plates), vessels, tubes, etc., to facilitate convenient transfer to individual wells or vessels for contacting cells, performing cell-free assays, etc. The library may be composed of molecules having common structural features which differ in the number or type of group attached to the main structure or may be completely random. Libraries include but are not limited to, for example, phage display libraries, peptide libraries, polysome libraries, aptamer libraries, synthetic small molecule libraries, natural compound libraries, and chemical libraries. Methods for preparing libraries of molecules are well known in the art and many libraries are available from commercial or non-commercial sources. Libraries of interest include synthetic organic combinatorial libraries. Libraries, such as, synthetic small molecule libraries and chemical libraries can comprise a structurally diverse collection of chemical molecules. Small molecules include organic molecules often having multiple carbon-carbon bonds. The libraries can comprise cyclic carbon or heterocyclic structure and/or aromatic or polyaromatic structures substituted with one or more functional groups. In some embodiments, the small molecule has between 5 and 50 carbon atoms, e.g., between 7 and 30 carbons. In some embodiments, the compounds are macrocyclic. Libraries of interest also include peptide libraries, randomized oligonucleotide libraries, and the like. Libraries can be synthesized of peptoids and non-peptide synthetic moieties. Such libraries can further be synthesized which contain non-peptide synthetic moieties which are less subject to enzymatic degradation compared to their naturally-occurring counterparts. Small molecule combinatorial libraries may also be generated. A combinatorial library of small organic compounds may comprise a collection of closely related analogs that differ from each other in one or more points of diversity and are synthesized by organic techniques using multi-step processes. Combinatorial libraries can include a vast number of small organic compounds. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Pat. No. 5,712,171. In some embodiments, mixtures containing two or more compounds, extracts or other preparations obtained from natural sources (which may comprise dozens of compounds or more), and/or inorganic compounds, etc., are screened.

In one embodiment, the methods of the invention are used to screen "approved drugs". An "approved drug" is any compound (which term includes biological molecules such as proteins and nucleic acids) which has been approved for use in humans by the FDA or a similar government agency in another country, for any purpose. This can be a particularly useful class of compounds to screen because it represents a set of compounds which are believed to be safe and, at least in the case of FDA approved drugs, therapeutic for at least one purpose. Thus, there is a high likelihood that these drugs will at least be safe for other purposes.

Representative examples of libraries that could be screened include DIVERSet™, available from ChemBridge Corporation, 16981 Via Tazon, San Diego, Calif. 92127. DIVERSet contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening. For descriptions of additional libraries, see, for example, Tan, et al., *Am. Chem. Soc.* 120, 8565-8566, 1998; Floyd C D, Leblanc C, Whittaker M, *Prog Med Chem* 36:91-168, 1999. Numerous libraries are commercially available, e.g., from AnalytiCon USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. For example, libraries based on quinic acid and shikimic acid, hydroxyproline, santonine, dianhydro-D-glucitol, hydroxypipecolinic acid, andrographolide, piperazine-2-carboxylic acid based library, cytosine, etc., are commercially available.

In some embodiments. the candidate agents are cDNAs from a cDNA expression library prepared from cells, e.g., pluripotent cells. Such cells may be embryonic stem cells, oocytes, blastomeres, teratocarcinomas, embryonic germ cells, inner cell mass cells, etc.

It will be appreciated that the candidate reprogramming agent to be tested is typically one that is not present in standard culture medium, or if present is present in lower amounts than when used in the present invention.

It will also be appreciated that a useful reprogramming agent or other form of reprogramming treatment need not be capable of reprogramming all types of somatic cells and need not be capable of reprogramming all somatic cells of a given cell type. Without limitation, a candidate agent that results in a population that is enriched for reprogrammed cells by a factor of 2, 5, 10, 50, 100 or more (i.e., the fraction of reprogrammed cells in the population is 2, 5, 10, 50, or 100 times more than present in a starting population of cells treated in the same way but without being contacted with the candidate agent) is of use.

In some embodiments of the invention, the inventive screening method is used to identify an agent or combination of agents that substitutes for Klf4 in reprogramming cells to an ES-like state. The method may be practiced using somatic cells engineered to express Sox2 and Oct4 and contacted with a Wnt pathway activator. In some embodiments, the method is used to identify an agent that substitutes for Sox2 in reprogramming cells to an ES-like state. The method may be practiced using somatic cells engineered to express Klf4 and Oct4 and contacted with a Wnt pathway activator. In some embodiments, the method is used to identify an agent that substitutes for Oct4 in reprogramming cells to an ES-like state. The method may be practiced using somatic cells engineered to express Sox2 and Klf 4 and contacted with a Wnt pathway activator. It is contemplated that engineered expression of Klf4, Sox2, Oct4, and c-Myc is replaced by treating somatic cells with a combination of small molecules and/or polypeptides or other agents that do not involve modification of the genome. In some embodiments, the methods are practiced using human cells. In some embodiments, the methods are practiced using mouse cells. In some embodiments, the methods are practiced using non-human primate cells.

The invention encompasses testing Wnt pathway modulators, e.g., libraries of small molecules known or suspected to modulate the Wnt pathway, to identify those that are effective in enhancing reprogramming and/or have superior ability to enhance reprogramming somatic cells to pluripotency, e.g., relative to other compounds tested. In some embodiments, at least 10, at least 20, at least 50, at least 100, or at least 1,000 small molecules, e.g., structurally related molecules, at least some of which are known or believed to modulate Wnt pathway activity, are tested. In some embodiments, a Wnt inhibitor is used to confirm that a compound that enhances reprogramming and is suspected of doing so by modulating Wnt pathway activity does in fact act via the Wnt pathway. For example, if the Wnt pathway inhibitor blocks the effect of a test compound on reprogramming, it may be concluded that the test compound acts via the Wnt pathway.

The methods and compositions of the present invention relating to Wnt pathway modulation may be applied to or used in combination with various other methods and compositions useful for somatic cell reprogramming and/or for identifying reprogramming agents for use in somatic cell reprogramming. Such combined methods and compositions are aspects of the invention. For example, some embodiments of the invention employ cell types (e.g., neural stem cells or progenitor cells) that naturally express one or more reprogramming factors at levels higher than such factor(s) are expressed in many other cell types (see, e.g., Eminli, et al., Reprogramming of Neural Progenitor Cells into iPS Cells in the Absence of Exogenous Sox2 Expression, Stem Cells. 2008 Jul. 17., epub ahead of print).

The methods and compositions may be used together with methods and compositions disclosed in PCT/US2008/004516, which is incorporated herein by reference:

Genetically homogeneous 'secondary' somatic cells that carry reprogramming factors as defined doxycycline (dox)-inducible transgenes have been derived Wernig, et al., A novel drug-inducible transgenic system for direct reprogramming of multiple somatic cell types. Nature Biotechnology; published online 1 Jul. 2008; doi:10.1038/nbt1483). These cells were produced by infecting fibroblasts with dox-inducible lentiviruses, reprogramming by dox addition, selecting induced pluripotent stem cells and producing chimeric mice. Cells derived from these chimeras reprogram upon dox exposure without the need for viral infection with efficiencies 25- to 50-fold greater than those observed using direct infection and drug selection for pluripotency marker reactivation. In some embodiments of the invention, such secondary somatic cells are used in embodiments of the present invention and/or secondary somatic cells are generated without use of c-Myc virus by employing Wnt pathway stimulation as described herein. The instant invention contemplates use of Wnt pathway modulation in compositions and methods relating to secondary somatic cells.

In some embodiments of the invention, the somatic cells contain a nucleic acid sequence encoding a selectable marker, operably linked to a promoter of an endogenous pluripotency gene, e.g., Oct4 or Nanog. The sequence encoding the marker may be integrated into the genome at the endogenous locus. The selectable marker may be, e.g., a readily detectable protein such as a fluorescent protein, e.g., GFP or a derivative thereof. Expression of the marker is indicative of reprogramming and can thus be used to identify or select reprogrammed cells, quantify reprogramming efficiency, and/or to identify, characterize, or use agents that enhance reprogramming and/or are being tested for their ability to enhance reprogramming.

Reprogrammed Somatic Cells and Uses Thereof

The present invention provides reprogrammed somatic cells (RSCs), including induced pluripotent stem cells (iPS cells), produced by the methods of the invention. These cells have numerous applications in medicine, agriculture, and other areas of interest, some of which are described here.

The invention provides methods for the treatment or prevention of a condition in a mammal. In one embodiment, the methods involve obtaining somatic cells from the individual, reprogramming the somatic cells so obtained by methods of the present invention to obtain RSCs, e.g., iPS cells. The RSCs are then cultured under conditions suitable for their development into cells of a desired cell type. The developed cells of the desired cell type are introduced into the individual to treat the condition. In an alternative embodiment, the methods start with obtaining somatic cells from the individual, reprogramming the somatic cells so obtained by methods of the present invention. The RPCs are then cultured under conditions suitable for development of the RPCs into a desired organ, which is harvested and introduced into the individual to treat the condition. The condition may be any condition in which cell or organ function is abnormal and/or reduced below normal levels. Thus, the invention encompasses obtaining somatic cells from an individual in need of cell therapy, reprogramming the cells by a process that comprises activating a Wnt pathway and/or culturing the cells in Wnt conditioned medium, optionally differentiating reprogrammed somatic cells them to generate cells of one or more desired cell types, and introducing the cells into the individual. An individual in need of cell therapy may suffer from any condition, wherein the condition or one or more symptoms of the condition can be alleviated by administering cells to the donor and/or in which the progression of the condition can be slowed by administering cells to the individual. The method may include a step of identifying or selecting reprogrammed somatic cells and separating them from cells that are not reprogrammed.

The RSCs in certain embodiments of the present invention are ES-like cells, also referred to as iPS cells, and thus may be induced to differentiate to obtain the desired cell types according to known methods to differentiate ES cells. For example, the iPS cells may be induced to differentiate into hematopoietic stem cells, muscle cells, cardiac muscle cells, liver cells, pancreatic cells, cartilage cells, epithelial cells, urinary tract cells, nervous system cells (e.g., neurons) etc., by culturing such cells in differentiation medium and under conditions which provide for cell differentiation. Medium and methods which result in the differentiation of embryonic stem cells obtained using traditional methods are known in the art, as are suitable culturing conditions. Such methods and culture conditions may be applied to the iPS cells obtained according to the present invention. See, e.g., Trounson, A., The production and directed differentiation of human embryonic stem cells, Endocr Rev. 27(2):208-19, 2006 and references therein, all of which are incorporated by reference, for some examples. See also Yao, S., et al, Long-term self-renewal and directed differentiation of human embryonic stem cells in chemically defined conditions, Proc Natl Acad Sci USA, 103(18): 6907-6912, 2006 and references therein, all of which are incorporated by reference.

Thus, using known methods and culture medium, one skilled in the art may culture the reprogrammed pluripotent cells to obtain desired differentiated cell types, e.g., neural cells, muscle cells, hematopoietic cells, etc. The subject cells may be used to obtain any desired differentiated cell type. Such differentiated human cells afford a multitude of therapeutic opportunities. For example, human hematopoietic stem cells derived from cells reprogrammed according to the present invention may be used in medical treatments requiring bone marrow transplantation. Such procedures are used to treat many diseases, e.g., late stage cancers and malignancies such as leukemia. Such cells are also of use to treat anemia, diseases that compromise the immune system such as AIDS, etc. The methods of the present invention can also be used to treat, prevent, or stabilize a neurological disease such as Alzheimer's disease, Parkinson's disease, Huntington's disease, or ALS, lysosomal storage diseases, multiple sclerosis, or a spinal cord injury. For example, somatic cells may be obtained from the individual in need of treatment, and reprogrammed to gain pluripotency, and cultured to derive neurectoderm cells that may be used to replace or assist the normal function of diseased or damaged tissue.

Reprogrammed cells that produce a growth factor or hormone such as insulin, etc., may be administered to a mammal for the treatment or prevention of endocrine disorders. Reprogrammed epithelial cells may be administered to repair damage to the lining of a body cavity or organ, such as a lung, gut, exocrine gland, or urogenital tract. It is also contemplated that reprogrammed cells may be administered to a mammal to treat damage or deficiency of cells in an organ such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

The present invention has the potential to provide an essentially unlimited supply of genetically matched cells suitable for transplantation. Such a supply would address the significant problem associated with current transplantation methods, i.e., rejection of the transplanted tissue which may occur because of host versus graft or graft versus host rejection. RSCs may also be combined with a matrix to form a tissue or organ in vitro or in vivo that may be used to repair or replace a tissue or organ in a recipient mammal. For example, RSCs may be cultured in vitro in the presence of a matrix to produce a tissue or organ of the urogenital, cardiovascular, or musculoskeletal system. Alternatively, a mixture of the cells and a matrix may be administered to a mammal for the formation of the desired tissue in vivo. The RSCs produced according to the invention may be used to produce genetically engineered or transgenic differentiated cells, e.g., by introducing a desired gene or genes, or removing all or part of an endogenous gene or genes of RSCs produced according to the invention, and allowing such cells to differentiate into the desired cell type. One method for achieving such modification is by homologous recombination, which technique can be used to insert, delete or modify a gene or genes at a specific site or sites in the genome.

This methodology can be used to replace defective genes or to introduce genes which result in the expression of therapeutically beneficial proteins such as growth factors, hormones, lymphokines, cytokines, enzymes, etc. For example, the gene encoding brain derived growth factor maybe introduced into human embryonic or stem-like cells, the cells differentiated into neural cells and the cells transplanted into a Parkinson's patient to retard the loss of neural cells during such disease. Using known methods to introduced desired genes/mutations into ES cells, RSCs may be genetically engineered, and the resulting engineered cells differentiated into desired cell types, e.g., hematopoietic cells, neural cells, pancreatic cells, cartilage cells, etc. Genes which may be introduced into the RSCs include, for example, epidermal growth factor, basic fibroblast growth factor, glial derived neurotrophic growth factor, insulin-like growth factor (I and II), neurotrophin3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, collagen, human serum albumin, etc.

Negative selection systems known in the art can be used for eliminating therapeutic cells from a patient if desired. For example, cells transfected with the thymidine kinase (TK) gene will lead to the production of embryonic (e.g., ES-like) cells containing the TK gene. Differentiation of these cells will lead to the isolation of therapeutic cells of interest which also express the TK gene. Such cells may be selectively eliminated at any time from a patient upon gancyclovir administration. Such a negative selection system is described in U.S. Pat. No. 5,698,446. In other embodiments the cells are engineered to contain a gene that encodes a toxic product whose expression is under control of an inducible promoter. Administration of the inducer causes production of the toxic product, leading to death of the cells. Thus any of the somatic cells of the invention may comprise a suicide gene, optionally contained in an expression cassette, which may be integrated into the genome. The suicide gene is one whose expression would be lethal to cells. Examples include genes encoding diphtheria toxin, cholera toxin, ricin, etc. The suicide gene may be under control of expression control elements that do not direct expression under normal circumstances in the absence of a specific inducing agent or stimulus. However, expression can be induced under appropriate conditions, e.g., (i) by administering an appropriate inducing agent to a cell or organism or (ii) if a particular gene (e.g., an oncogene, a gene involved in the cell division cycle, or a gene indicative of dedifferentiation or loss of differentiation) is expressed in the cells, or (iii) if expression of a gene such as a cell cycle control gene or a gene indicative of differentiation is lost. See, e.g., U.S. Pat. No. 6,761,884. In some embodiments the gene is only expressed following a recombination event mediated by a site-specific recombinase. Such an event may bring the coding sequence into operable association with expression control elements such as a promoter. Expression of the suicide gene may be induced if it is desired to eliminate cells (or their progeny) from the body of a subject after the cells (or their ancestors) have been administered to a subject. For example, if a reprogrammed somatic cell gives rise to a tumor, the tumor can be eliminated by inducing expression of the suicide gene. In some embodiments tumor formation is inhibited because the cells are automatically eliminated upon dedifferentiation or loss of proper cell cycle control.

Examples of diseases, disorders, or conditions that may be treated or prevented include neurological, endocrine, structural, skeletal, vascular, urinary, digestive, integumentary, blood, immune, auto-immune, inflammatory, endocrine, kidney, bladder, cardiovascular, cancer, circulatory, digestive, hematopoietic, and muscular diseases, disorders, and conditions. In addition, reprogrammed cells may be used for reconstructive applications, such as for repairing or replacing tissues or organs. In some embodiments, it may be advantageous to include growth factors and proteins or other agents that promote angiogenesis. Alternatively, the formation of tissues can be effected totally in vitro, with appropriate culture media and conditions, growth factors, and biodegradable polymer matrices.

With respect to the therapeutic methods of the invention the administration of RSCs to a mammal is not limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. The RSCs may be administered to the mammal in a single dose or multiple doses. When multiple doses are administered, the doses may be separated from one another by, for example, one week, one month, one year, or ten years. One or more growth factors, hormones, interleukins, cytokines, or other cells may also be administered before, during, or after administration of the cells to further bias them towards a particular cell type.

The RSCs of the present invention may be used as an in vitro model of differentiation, in particular for the study of genes which are involved in the regulation of early development. Differentiated cell tissues and organs generated using the reprogrammed cells may be used to study effects of drugs and/or identify potentially useful pharmaceutical agents.

Further Applications of Somatic Cell Reprogramming Methods and Reprogrammed Cells The reprogramming methods disclosed herein may be used to generate RSCs, e.g., iPS cells, for a variety of animal species. The RSCs generated can be useful to produce desired animals. Animals include, for example, avians and mammals as well as any animal that is an endangered species. Exemplary birds include domesticated birds (e.g., quail, chickens, ducks, geese, turkeys, and guinea hens). Exemplary mammals include murine, caprine, ovine, bovine, porcine, canine, feline and non-human primate. Of these, preferred members include domesticated animals, including, for examples, cattle, pigs, horses, cows, rabbits, guinea pigs, sheep, and goats.

Methods for Gene Identification

The invention provides methods for identifying a gene whose expression inhibits generation of reprogrammed cells. One method comprises: (i) activating the Wnt pathway in somatic cells; (ii) reducing expression of a candidate gene by RNAi; (iii) determining whether reducing expression of the candidate gene results in increased efficiency of reprogramming and, if so, identifying the candidate gene as one whose expression inhibits reprogramming of somatic cells. One method comprises: (i) culturing somatic cells in Wnt conditioned medium; (ii) reducing expression of a candidate gene by RNAi; (iii) determining whether reducing expression of the candidate gene results in increased efficiency of reprogramming and, if so, identifying the candidate gene as one whose expression inhibits reprogramming of somatic cells. Optionally the somatic cells are engineered to express at least one gene selected from: Oct4, Sox2, Nanog, Lin28, and Klf4. Optionally the cells are contacted with Wnt pathway modulator. Libraries of shRNA or siRNA of use in the method are commercially available. The identified gene is a target for inhibition in order to enhance cellular reprogramming. Agents that inhibit the gene (either RNAi agents or other agents such as small molecules) are of use to reprogram somatic cells, e.g., in conjunction with a Wnt activator.

EXEMPLIFICATION

The invention now being generally described, it will be more readily understood by reference to the following example, which are included merely for purposes of illustration of certain aspects and embodiments of the present invention, and are not intended to limit the invention.

Materials and Methods for Example 1

Cell culture, viral infections, induction of gene expression. Cells were cultured in 15% FBS, DMEM-KO, Penn/Step, Glutamine, Nonessential amino acids, β-ME, and LIF. Mouse embryo fibroblasts (MEFs) with an Oct4-IRES-eGFP construct (Meissner, A., et al., Nature Biotechnology, Direct reprogramming of genetically unmodified fibroblasts into pluripotent stem cells. Published online: 27 Aug. 2007|doi: 10.1038/nbt1335) inserted into the endogenous Oct4 locus were infected with lentiviral vectors driving the doxycycline-inducible expression of Oct4, Sox2, Klf4 and c-Myc or only Oct4, Sox2, and Klf4. The vectors were based on the FUGW lentiviral vector backbone (Lois C, et al., Science 2002; 295: 868-872.), modified to include a tet-inducible promoter. Two days following infection cells were split and induced with doxycycline in the presence or absence of Wnt3a conditioned media (used in a 1:1 dilution with normal ES media with 2×LIF). These cells were monitored for GFP expression by flow cytometry at day 13 and again at day 20. In parallel, MEFs with doxycycline-inducible Oct4 expressed from the collagen locus and Oct4-IRES-(neo resistance) inserted into the endogenous Oct4 locus were infected with lentiviruses driving the overexpression of either Sox2, Klf4 and c-Myc or Sox2 and Klf4. Again, two days following infection cells were split and induced with doxycycline in the presence or absence of Wnt3a conditioned media. Separate plates of these cells were selected with G418 at day 7 and day 13 respectively. Following at least one week of G418 selection, resistant colonies were examined and counted.

Conditioned medium. Wnt 3a conditioned media (CM) was collected from mouse L cells that had been transfected with Wnt3a cDNA (Shibamoto et al. 1998). These cells are available through ATCC(CRL-2647) along with the untransfected parent cell line (CRL-2648) to use for control conditioned medium. Wnt3a transfected cells secrete Wnt, reaching levels up to 400 ng/mL of the Wnt3a protein in their growth media. The basal medium consisted of DMEM, 15% FBS, Penn/Strep, Glutamine and nonessential amino acids, prepared according the protocol of Singla et al. (Singla, et al., Biochem Biophys Res Commun., 345(2):789-95, 2006). The media collected from the secreting fibroblasts was filtered and diluted 1:1 with regular ES cell media (15% FBS, DMEM-KO, Penn/Step, Glutamine, Nonessential amino acids, β-ME, and LIF). This media was then used to treat ES cells. The Wnt3a conditioned media has been shown by Applicants and others to activate the Wnt signaling pathway in ES cells, as demonstrated by immunoblots examining beta-catenin phosphorylation.

Example 1

Generation of ES-Like Cells Using Wnt3a Conditioned Media

We hypothesized that stimulation of the stimulation of the Wnt pathway using soluble factors could modulate the efficiency of inducing pluripotency in somatic cells. This Example describes initial experiments undertaken to determine the effect of Wnt pathway stimulation on reprogramming. Cells containing an Oct4-IRES-eGFP or Oct4-IRES-neo construct were infected with lentiviral vectors encoding either three or four factors as described above. Expression of the pluripotency factors was induced on day 2. In some experiments, cells were cultured in Wnt3a conditioned media or unconditioned media as shown in FIG. 4A (top) from days 2-13. GFP expression was analyzed by FACS on day 13 and 20. In other experiments, cells were cultured in Wnt3a conditioned media or unconditioned media as shown in FIG. 4A (bottom) from days 2-13 or 2-20. G418 selection was imposed on day 7 or 13. Surviving colonies were counted on day 20.

Results showed that Wnt 3a conditioned media increases the rate of iPS formation in fibroblasts transduced with the four reprogramming transcription factors. As shown in FIG. 4B, Wnt3a promotes iPS cell formation in cells over-expressing Oct4, Sox2, Klf4 and c-Myc. Selectable cells overexpressing Oct4, Sox2, Klf4 and c-Myc formed robust G418-resistant colonies earlier in the presence of Wnt3a conditioned media than in the absence of this media. When selected at day 7, only small colonies formed in the absence of Wnt, none of which could be propagated in culture. Colonies formed in the presence of Wnt conditioned media at this point were larger and could be passaged as clones. When selection was started at day 13, colonies were observed in the absence of Wnt3a conditioned medium that could be propagated. Although there were fewer colonies at this time point in the presence of Wnt conditioned media than in the absence of Wnt conditioned media, the colonies that did form were large, relatively homogenous in appearance and again could be maintained in culture. This result suggests that Wnt3a conditioned medium not only increased the rate of reprogramming but also selected for colonies of reprogrammed cells.

Wnt3a conditioned media also allows iPS cells to be formed without addition of the oncogenic transcription factor c-Myc. Whereas no iPS cells were formed in our initial experiment when fibroblasts were transduced with Oct4, Sox2 and Klf4, we did observe iPS colonies with these three factors when cells were grown in Wnt3a conditioned media. These colonies appear to be true iPS cells based on morphology and activation of the endogenous Oct4 locus, an event normally restricted to pluripotent cells. As shown in FIG. 4C, in the presence of Wnt3a conditioned media, robust neo-resistant colonies were observed in Oct4, Sox2, Klf4 overexpressing cells selected at both day 7 and day 13. In the absence of Wnt conditioned media, no cells not infected with c-Myc virus were found to be neo-resistant at either time point. Without selection, Oct4-IRES-eGFP cells infected with Sox2 and Klf4 lentivirus were found to express GFP (indicative of activation of the endogenous Oct4 locus) by day 20 only in the presence of Wnt conditioned media.

Discussion

The findings described above are significant for at least two major reasons. First, there is great interest in creating iPS cells that do not have viral integrations of the oncogenic c-Myc transcription factor. Chimaeric mice with iPS cells made with Myc show high rates of cancer associated with somatic reactivation of the c-Myc virus. Even in vitro we note that iPS cell lines generated with the c-Myc virus contain a mixed population with some cells appearing morphologically much like ES cells and others growing more like transformed, cancerous cells. Our results obtained thus far indicate that iPS lines created without c-Myc in Wnt3a conditioned media appear to be more homogeneously ES-like in their morphology. Second, Wnt3a conditioned media appears to exert a selective effect favoring the formation of large, homogenous colonies. Use of Wnt3a conditioned medium or Wnt3a pathway activators could thus be used as an alternative selection process rather than imposing a selection step that requires genetic modification of the initial somatic cells. Use of Wnt3a conditioned medium or Wnt3a pathway activators during reprogramming would thus provide a valuable improvement to any method of reprogramming somatic cells currently known in the art or developed in the future.

Materials and Methods for Examples 2-8

Cell Culture.

V6.5 (C57BL/6-129) murine ES cells and iPS cells were grown under typical ES conditions on irradiated mouse embryonic fibroblasts (MEFs). Transgenic MEFs used in the infections with DOX-inducible lentiviruses (T. Brambrink, R. Foreman, *Cell Stem Cell* 2, 151-159 (2008)) were harvested at 13.5 dpc and selected on 2 ug/ml puromycin from embryos after blastocyst injection of Oct4-IRES-GFPneo/Oct4-inducible ES cells (M. Wernig, A. Meissner, *Nature* 448, 318-324 (2007).) or harvested from F1 matings between R26-M2rtTA mice (C. Beard, K. Hochedlinger, *Genesis* 44, 23-28 (2006)) and Oct4-GFP mice (A. Meissner, M. Wernig, Nat Biotechnol 25, 1177-1181 (2007). Wnt3a conditioned media and control conditioned media was generated according to standard protocols (ATCC) (K. Willert, J. D. Brown, *Nature* 423, 448-452 (2003), described also above) and used in a 1:1 ratio with standard ES cell medium). Wnt inhibitor ICG-001 was dissolved in DMSO to a stock concentration of 0.1M. The final, working concentration of the Wnt inhibitor was 4 uM.

Viral Transduction.

Tetracycline inducible lentiviral constructs expressing the cDNAs for Oct4, Klf-4, Sox2 and c-Myc were used as previously described (Brambrink, supra). Virus was prepared by transfecting HEK293T cells with a mixture of viral plasmid and packaging constructs expressing the viral packaging functions and the VSV-G protein (Fugene, Roche). Medium was replaced 24 hours after transfection and viral supernatants were collected at 48 hours and 72 hours. After filtration, supernatants were pooled and $2.5 \times 10^5$ MEFs were incubated with viral supernatants and fresh media at a ratio of 1:1 for 24 hours. Infected cells were then split at ratios from 1:5 to 1:12 onto gelatin-coated 10 cm dishes. One day following the split, ES media was supplemented with 2 ug/ml DOX and, in the appropriate dishes, conditioned media and/or chemical inhibitor.

Immunostaining and Antibodies Cells were stained as described previously (Wernig, supra). Antibodies against Nanog (Bethyl) and SSEA1 (R&D systems, Minneapolis, Minn.) were used according to supplier recommendations.

Teratoma Formation

Teratoma formation was assayed as previously described. Briefly, cells were trypsinized and $5 \times 10^5$ cells were injected subcutaneously into SCID mice. After 14-21 days, teratomas were dissected, fixed in 10% phosphate-buffered formalin overnight and subsequently embedded in paraffin wax using a Tissue-Tek VIP embedding machine (Miles Scientific, Naperville, Ill.) and a Thermo Shandon Histocenter 2 (Thermo Fisher Scientific, Waltham, Mass.). Sections were cut at a thickness of 2 μm using a Leica RM2065 (Leica, Wetzlar, Germany) and stained with hematoxylin and eosin (K. Hochedlinger, Y. Yamada, Cell 121, 465-477 (2005).

Blastocyst Injection. Injections of iPS cells into Balb/c host blastocysts were carried out as previously described (Beard, supra).

Example 2

Further Experiments Relating to Generation of ES-Like Cells Using Wnt3a Conditioned Media To further define the effect of Wnt3a on reprogramming, we infected MEFs that harbor a doxycyline (DOX)-inducible Oct4 cDNA (Hochedlinger, 2005) with DOX-inducible lentiviral vectors encoding Sox2, Klf4, and c-Myc (Brambrink, et al., 2008). These cells also contained a G418 resistance cassette in the endogenous Oct4 locus allowing for drug selection of iPS cells (Meissner et al., 2007).

Four-factor expression was induced by addition of DOX in cells cultured in the presence or absence of Wnt3a conditioned medium (Wnt3a-CM), G418 selection was initiated after 5 days and the number of drug resistant colonies was determined 24 days after induction (FIG. 1a). FIG. 1b shows that the total number of drug resistant colonies was increased more that 7 fold when the cells were cultured in Wnt3a-CM. We also noted that the drug resistant colonies were larger and more ES-cell like by morphology when cultured in Wnt3a-CM than in ES cell medium (FIG. 1c). Furthermore, the colonies that appeared in Wnt3a-CM with G418 selection initiated on Day 5 could be further propagated, in contrast to the small colonies derived in standard ES cell medium.

Given that Wnt3a-CM had a positive effect on reprogramming in concert with the four transcription factors, we next examined if Wnt3a-CM could substitute for any of the nuclear factors. In parallel experiments, fibroblasts were transduced with subsets of the transcription factors and observed in the presence and absence of Wnt3a-CM (FIGS. 1d and 1e). No resistant colonies formed in the absence of Oct4 or Klf4 infection. One colony was observed in the absence of Sox2 retrovirus, but this colony could not be not be further propagated in ES cell culture conditions. In contrast, in the presence of Wnt3a-CM, multiple robust G418-resistant colonies formed in the absence of c-Myc in cells over-expressing Oct4, Sox2 and Klf4 (FIGS. 1d and 1e). Similar to colonies from MEFs transduced with all four factors, these iPS lines could be propagated in standard ES cell media without further selection and retained ES cell morphology. In replicate experiments, G418-resistant colonies were formed occasionally with no c-Myc transduction in the absence Wnt3a-CM. However, consistent with published reports (8,9), these colonies were rare. In the following, iPS cells generated with only three factors and without c-Myc will be designated as $Myc^{[-]}$ iPS cells.

To more closely examine the effects of Wnt3a-CM treatment on the reprogramming process, Oct4/Sox2/Klf4 and Oct4/Sox2/Klf4/c-Myc over-expressing MEFs were cultured with and without and Wnt3a-CM, and G418 selection was initiated at different times after DOX addition. FIG. 1f shows that when three factor over-expressing cells were cultured in Wnt3a-CM medium about 3 fold more $Myc^{[-]}$ iPS colonies appeared when G418 was added at day 5 and about 20 fold more colonies when G418 was added at day 10 after induction as compared to cultivation in ES cell medium (FIG. 1f, left panel). Wnt3a-CM medium also increased the number of drug resistant colonies after induction of all four factors, though the fold increase was less pronounced than in three factor induced cells (FIG. 1f, right panel). These results indicate that Wnt3a-CM increased the number of drug resistant colonies in both three factor and four factor induced cells, with the most pronounced effect on three factor over-expressing cells with selection applied at the later time point.

Example 3

Generation of $Myc^{[-]}$ iPS Clones without Genetic Selection

Recently, iPS cells have been generated without c-Myc retrovirus (Myc[−]), but in the absence of exogenous c-Myc the efficiency and kinetics of reprogramming are significantly reduced (Nakagawa et al., 2008; Wernig et al., 2008). We tested whether Wnt3a-CM would also aid in the generation of iPS cells in the absence of selection for Oct4 reactivation. For this, cells with GFP driven by the endogenous Oct4 promoter were utilized (Meissner, et al., 2008). Oct4/Sox2/Klf4 infected cells with and without Wnt3a-CM treatment were analyzed for GFP expression by flow cytometry at days 10, 15 and 20 after DOX induction. No GFP positive cells were present with or without Wnt3a-CM treatment on day 10 or day 15. By day 20 a small population of GFP expressing cells was detected in cells cultured in Wnt3a-CM but not in standard ES cell medium (FIG. 1g). The Wnt3a-CM exposed cultures formed GFP expressing colonies with morphology typical for ES or iPS cells (FIG. 1h). However, unlike four factor transduced cells, which usually form a highly heterogeneous population of cells when propagated without selection, the Oct4/Sox2/Klf4/Wnt3a-CM colonies appeared homogenously ES-like similar to previously reported $Myc^{[-]}$ iPS clones (Nakagawa, et al., 2008.

Example 4

Developmental Potential of Myc[−] iPS Cells Derived with Wnt3a-CM

Figure 2:
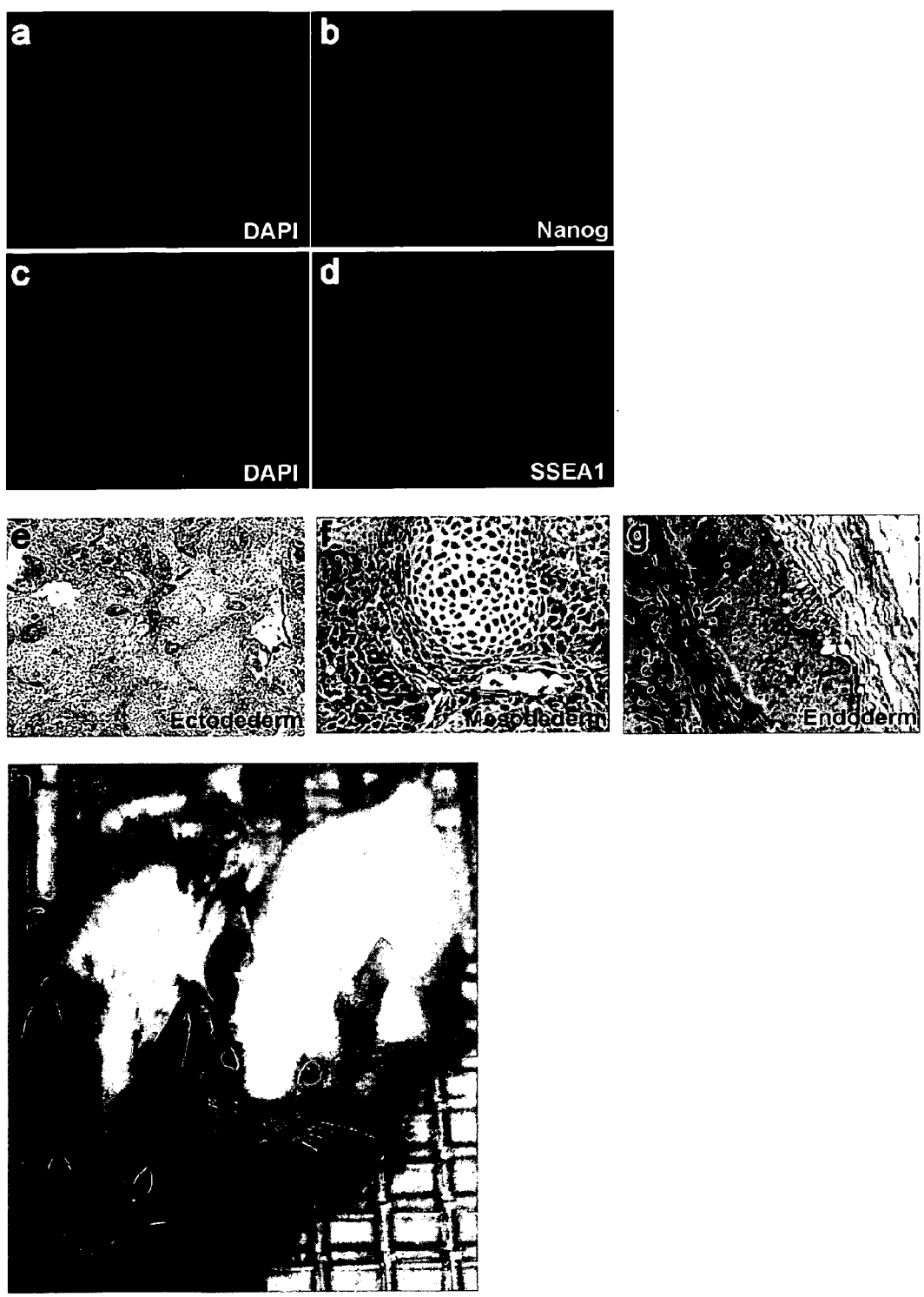
FIG. 2. Induction of Pluripotency in Wnt Stimulated cells. a-d. Immunostaining reveals induction of pluripotency markers, Nanog (a-b) and SSEA-1(c-d) in Wnt3a-CM treated Myc[−] cells. e-g. Wnt3a-CM treated Myc[−] lines formed teratomas when injected into SCID mice subcutaneously. Teratomas from Oct4/Sox2/Klf4/Wnt3aCM iPS lines showed evidence of differentiated cells of three germ layers similar to teratomas formed from V6.5 mES injections. Arrows indicated neural tissue in (e), cartilage in (f), and endodermal cells in (g), h. Oct4/Sox2/Klf4/Wnt3aCM iPS lines derived without selection gave rise to chimeric mice (as shown on the left) with agouti coat color and pigmented eyes (in contrast to wild type Balb/c mouse, right) providing evidence of contribution to somatic cells. Coat color of offspring confirmed that the Oct4/Sox2/Klf4/Wnt3aCM iPS line generated here is germline-competent (data not shown).

Several assays were performed to characterize the developmental potential of Myc[−] iPS cells derived with Wnt3a-CM treatment. Immunocytochemistry confirmed the expression of markers of pluripotency, including the nuclear factor Nanog (FIGS. 2a and 2b), and the surface glycoprotein SSEA1 (FIGS. 2c and 2d). Functional assays confirmed that, like ES cells, these iPS cells were pluripotent. When injected into SCID mice subcutaneously, the Myc[−] iPS cells gave rise to teratomas with histological evidence of cells differentiating into all three germ layers (FIGS. 2e, 2f and 2g). More importantly, Myc[−] iPS cells derived with Wnt3a-CM treatment contributed to the formation of differentiated tissues in chimeric mice (FIG. 2h). These results indicate that Wnt3a-CM treated Myc[−] clones are pluripotent cells that are morphologically and functionally indistinguishable from ES cells.

Example 5

Figure 3:
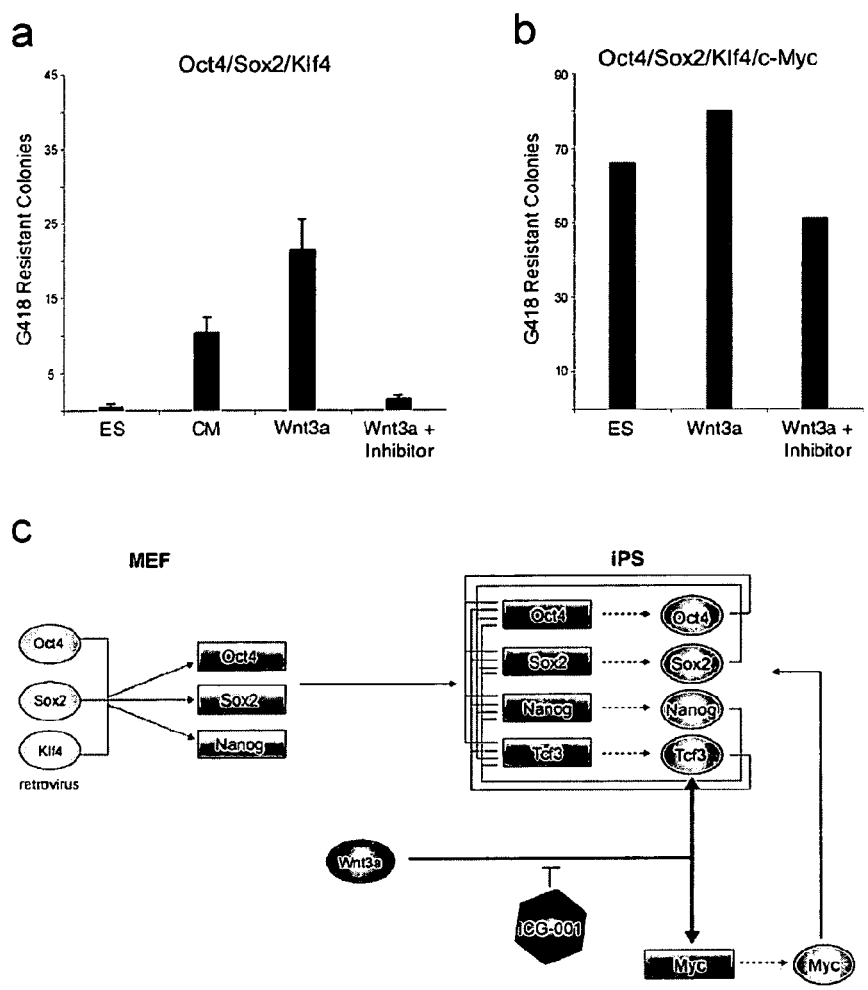
FIG. 3. Wnt/β-catenin stimulation enhances iPS colony formation in absence of c-Myc retrovirus. a. Counts are shown for G418 resistant colonies in Oct4/Sox2/Klf4 overexpressing MEFs cultured in ES cell media, MEF conditioned media, Wnt3a over-expressing conditioned media, and Wnt3a over-expressing conditioned media with ICG001 (4 µM). Selection was initiated on day 15 post-induction, and colonies were assessed on day 28. Wnt3a-CM treatment was maintained until day 22. Mean number of counts from triplicate experiments is displayed with error bars indicating S.D. b. Counts are shown for G418 resistant colonies (in a 32-cm$^2$ area) in Oct4/Sox2/Klf4/c-Myc over-expressing MEFs cultured in ES cell media, Wnt3a over-expressing conditioned media, and Wnt3a over-expressing conditioned media with ICG-001 (4 µM). Selection was initiated on day 10 post-induction, Wnt3a-CM was maintained until day 17, and colonies were assessed on day 20. c. Wnt stimulation promotes the formation of iPS cells in the absence of c-Myc transduction. This could be due to: i) direct regulation by the Wnt pathway of key endogenous pluripotency factors, such as Oct4, Sox2 and Nanog as suggested by genomic studies in ES cells (Cole et al., 2008), ii) Wnt pathway-induced activation of endogenous Myc (He et al., 1998; Cole et al., 2008), or other cell proliferation genes, accelerating the sequential process of forming iPS colonies.

Effect of Small Molecule Wnt Pathway Inhibitor on Generation of Ips Myc[−] and Ips Cells in the Presence of Wnt3a-CM To quantify the effects of Wnt3a-CM, triplicate experiments were performed on Oct4/Sox2/Klf4-inducible, G418 selectable MEFs (FIG. 3a). G418 was added to the cultures at 15 days after infection to select for cells that had reactivated the Oct4 locus. When scored on day 28 after infection, only a few Myc[−] G418 resistant colonies (between 0-3 colonies forming on each ten centimetre plate) were detected in standard ES cell culture conditions. In contrast, ~20 fold more drug resistant colonies formed when G418 selection was initiated on Wnt3a-CM-treated cells, consistent with the conclusion that activation of the Wnt pathway enhances reprogramming. It should be noted that conditioned medium from control fibroblasts lacking Wnt3a over-expression also caused a moderate increase in the number of G418-resistant colonies relative to standard ES medium, suggesting that normal fibroblasts may secrete factors, perhaps including Wnt3a, that promote reprogramming.

Figure 5:
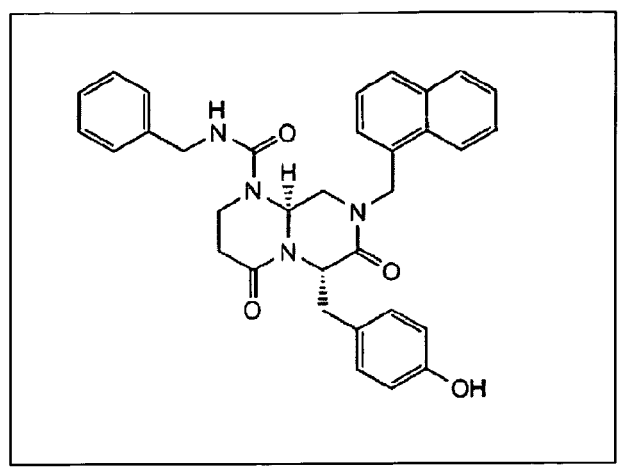
FIG. 5. Structure of ICG-001.

To independently assess the effect of Wnt3a on reprogramming, we cultured cells in the presence of ICG-001 (Teo et al., 2005; McMillan and Kahn, 2005; see FIG. 5), an inhibitor of the Wnt/β-catenin pathway. FIG. 3a (right columns) shows that 4 µM ICG-001 strongly inhibited the effect of Wnt3a-CM on Myc[−] iPS formation. The effects of Wnt3a-CM and ICG-001 were also examined in MEFs over-expressing all four reprogramming factors, including c-Myc (FIG. 3b). High numbers of G418 resistant colonies were observed in both standard ES cell media and Wnt3a-CM in four factor reprogrammed cells, with only a subtle increase in the number of colonies with Wnt3aCM. In contrast to the dramatic effect of ICG-001 on Myc cells, at the same dose, the compound had only a subtle effect on the number of G418 colonies in c-Myc transduced cells, and a relatively high number of resistant colonies were observed under these conditions. At higher doses of ICG-001, iPS colony numbers were further reduced, but even at 25 µM multiple Oct4/Sox2/Klf4/c-Myc iPS colonies were observed (data not shown). These results are consistent with the notion that Wnt3a can, at least in part, replace the role of c-Myc in reprogramming.

The Wnt signaling pathway has been shown to connect directly to the core transcriptional regulatory circuitry of ES cells, suggesting a mechanism by which this pathway could directly promote the induction of the pluripotency in the absence of c-Myc transduction (FIG. 3c). The Wnt signaling pathway has been shown to connect directly to the core transcriptional regulatory circuitry of ES cells, suggesting a mechanism by which this pathway could directly promote the induction of the pluripotency in the absence of c-Myc transduction (FIG. 2c). In ES cells, Tcf3 occupies and regulates the promoters of Oct4, Sox2 and Nanog (Cole et al., 2008; Tam et al., 2008; Yi et al., 2008). In MEFs, these endogenous pluripotency transcription factors are silenced. During reprogramming, as exogenous Oct4, Sox2 and Klf4 contribute to the reactivation of the endogenous pluripotency factors (Jaenisch and Young, 2008), Wnt signaling could directly potentiate the effect of these transcription factors, as it does in ES cells (Cole et al., 2008). Additionally or alternately, Wnt could serve to activate endogenous c-Myc directly, thereby substituting for exogenous c-Myc. Indeed, c-Myc is a well-established target of the Wnt pathway in colorectal cancer cells (He et al., 1998). In ES cells, Tcf3 occupies the c-Myc promoter, and Wnt3a positively contributes to expression of the gene (Cole et al., 2008). The fact that enforced over-expression of c-Myc counteracts the negative effect of the Wnt inhibitor ICG-001 on the reprogramming process suggests that Wnt stimulation could be acting upstream of the endogenous Myc. Wnt-induced effects on cell proliferation, mediated by c-Myc or other endogenous proliferation factors, could help to accelerate the sequence of events that lead to the generation of Myc[−] iPS colonies.

A major goal of current research is to identify transient cues that can reprogram somatic cells, eliminating the need for retroviruses. The studies described here establish that Wnt stimulation can be used to enhance the efficiency of reprogramming in combination with nuclear factors, Oct4, Sox2 and Klf4. By enhancing the efficiency of reprogramming in the absence of c-Myc retrovirus, soluble Wnt or small molecules that modulate the Wnt signaling pathway will likely prove useful in combination with other transient cues that can replace the remaining retroviruses.

Example 6

Identification of Additional Reprogramming Agents

Example 3 is modified in that the medium further contains, in addition to Wnt3a-CM, a candidate reprogramming agent to be tested for its potential to enhance or inhibit reprogramming. In some embodiments the cells are infected so that they express only 2 of the following 3 reprogramming factors: Oct4, Klf4, and Sox2. Agents that enhance generating of reprogrammed cells (e.g., increase speed or efficiency of reprogramming) are identified. The process is repeated to identify agents capable of substituting for engineered expression of Oct4, Klf4, and/or Sox2 in reprogramming somatic cells.

Example 7

Identification of Additional Reprogramming Agents

Example 3 is modified in that the Wnt3a-CM medium further contains a candidate reprogramming agent. In some embodiments, the cells are infected so that they express only 1 or 2 of the following reprogramming factors: Oct4, Lin28, Sox2, and Nanog (e.g., Oct4 only, Oct-4 and Sox2). Agents that enhance generating of reprogrammed cells are identified. The process is repeated to identify agents capable of substituting for engineered expression of Oct4, Lin28, Sox2, and/or Nanog in reprogramming somatic cells.

Example 8

Use of Small Molecule Wnt Pathway Modulator in Reprogramming

Example 3 is repeated except that instead of using Wnt3a-CM, ES cell medium containing a small molecule Wnt pathway activator is used.

References

Brambrink, T., Foreman, R., Welstead, G. G., Lengner, C. J., Wernig, M., Suh, H., and Jaenisch, R. (2008). Sequential expression of pluripotency markers during directreprogramming of mouse somatic cells. Cell Stem Cell 2, 151-159.
Cai, L., Ye, Z., Zhou, B. Y., Mali, P., Zhou, C., and Cheng, L. (2007). Promoting humanembryonic stem cell renewal or differentiation by modulating Wnt signal and culture conditions. Cell Res 17, 62-72.
Cole, M. F., Johnstone, S. E., Newman, J. J., Kagey, M. H., and Young, R. A. (2008). Tcf3 is an integral component of the core regulatory circuitry of embryonic stem cells. Genes and Development 15; 22(6):746-55 (2008).
Hanna, J., Wernig, M., Markoulaki, S., Sun, C. W., Meissner, A., Cassady, J. P., Beard, C., Brambrink, T., Wu, L. C., Townes, T. M., and Jaenisch, R. (2007). Treatment of sickle cell anemia mouse model with iPS cells generated from autologous skin. Science 318, 1920-1923.
He, T. C., Sparks, A. B., Rago, C., Hermeking, H., Zawel, L., da Costa, L. T., Morin, P. J., Vogelstein, B., and Kinzler, K. W. (1998). Identification of c-MYC as a target of the APC pathway. Science 281, 1509-1512.
Hochedlinger, K., Yamada, Y., (2005) Cell. 121, 465-477.
Jaenisch, R., and Young, R. A. (2008). Stem cells, the molecular circuitry of pluripotency and nuclear reprogramming. Cell 132, 567-582.
Kim, J., Chu, J., Shen, X., Wang, J., and Orkin, S. H. (2008). An extended transcriptional network for pluripotency of embryonic stem cells. Cell 132, 1049-1061.
Knoepfler, P. S. (2008). Why Myc? An unexpected ingredient in the stem cell cocktail. Cell Stem Cell 2, 18-21.
McMillan, M., and Kahn, M. (2005). Investigating Wnt signaling: a chemogenomic safari. Drug Discov Today 10, 1467-1474.
Meissner, A., Wernig, M., and Jaenisch, R. (2007). Direct reprogramming of genetically unmodified fibroblasts into pluripotent stem cells. Nat Biotechnol 25, 1177-1181.
Nakagawa, M., Koyanagi, M., Tanabe, K., Takahashi, K., Ichisaka, T., Aoi, T., Okita, K., Mochiduki, Y., Takizawa, N., and Yamanaka, S. (2008). Generation of induced pluripotent stem cells without Myc from mouse and human fibroblasts. Nat Biotechnol 26, 101-106.
Ogawa, K., Nishinakamura, R., Iwamatsu, Y., Shimosato, D., and Niwa, H. (2006). Synergistic action of Wnt and LIF in maintaining pluripotency of mouse ES cells. Biochem Biophys Res Commun 343, 159-166.
Okita, K., Ichisaka, T., and Yamanaka, S. (2007). Generation of germline-competent induced pluripotent stem cells. Nature 448, 313-317.
Reya, T., and Clevers, H. (2005). Wnt signalling in stem cells and cancer. Nature 434, 843-850.
Sato, N., Meijer, L., Skaltsounis, L., Greengard, P., and Brivanlou, A. H. (2004). Maintenance of pluripotency in human and mouse embryonic stem cells through activation of Wnt signaling by a pharmacological GSK-3-specific inhibitor. Nat Med 10, 55-63.
Singla, D. K., Schneider, D. J., LeWinter, M. M., and Sobel, B. E. (2006). wnt3a but not wnt11 supports self-renewal of embryonic stem cells. Biochem Biophys Res Commun 345, 789-795.
Stadtfeld, M., Maherali, N., Breault, D. T., and Hochedlinger, K. (2008). Defining molecular cornerstones during fibroblast to iPS cell reprogramming in mouse. Cell Stem Cell in press.
Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.
Takahashi, K., and Yamanaka, S. (2006). Induction of pluripotent stem cells from mouse embryonic and adult fibroblast cultures by defined factors. Cell 126, 663-676.
Tam, W. L., Lim, C. Y., Han, J., Zhang, J., Ang, Y. S., Ng, H. H., Yang, H., and Lim, B. (2008). Tcf3 Regulates Embryonic Stem Cell Pluripotency and Self-Renewal by the Transcriptional Control of Multiple Lineage Pathways. Stem Cells.
Teo, J. L., Ma, H., Nguyen, C., Lam, C., and Kahn, M. (2005). Specific inhibition of CBP/beta-catenin interaction rescues defects in neuronal differentiation caused by a presenilin-1 mutation. Proc Natl Acad Sci USA 102, 12171-12176.
Wernig, M., Meissner, A., Cassady, J. P., and Jaenisch, R. (2008). c-Myc is dispensable for direct reprogramming of mouse fibroblasts. Cell Stem Cell 2, 10-12.
Willert, K., Brown, J. D., Danenberg, E., Duncan, A. W., Weissman, I. L., Reya, T., Yates, J. R., 3rd, and Nusse, R. (2003). Wnt proteins are lipid-modified and can act as stem cell growth factors. Nature 423, 448-452.
Yi, F., Pereira, L., and Merrill, B. J. (2008). Tcf3 Functions as a Steady State Limiter of Transcriptional Programs of Mouse Embryonic Stem Cell Self Renewal. Stem Cells.
Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

* * *

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example Current Protocols in Cell Biology, ed. by Bonifacino, Dasso, Lippincott-Schwartz, Harford, and Yamada, John Wiley and Sons, Inc., New York, 1999; Manipulating the Mouse Embryos, A Laboratory Manual, 3$^{rd}$ Ed., by Hogan et al., Cold Spring Contain Laboratory Press, Cold Spring Contain, New York, 2003; Gene Targeting: A Practical Approach, IRL Press at Oxford University Press, Oxford, 1993; and Gene Targeting Protocols, Human Press, Totowa, N.J., 2000. All patents, patent applications and references cited herein are incorporated in their entirety by reference.

One skilled in the art readily appreciates that the present invention is well adapted to carry out the objects and obtain the ends and advantages mentioned, as well as those inherent therein. The methods, systems and kits are representative of certain embodiments, are exemplary, and are not intended as limitations on the scope of the invention. Modifications therein and other uses will occur to those skilled in the art. These modifications are encompassed within the spirit of the invention and are defined by the scope of the claims. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention can be explicitly excluded from the claims, regardless of whether the specific exclusion is recited in the specification. For example, any Wnt modulator, e.g., any Wnt pathway activating agent, any somatic cell type, any reprogramming agent, etc., may be excluded.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" is intended to encompass numbers that fall within a range of ±10% of a number, in some embodiments within ±5% of a number, in some embodiments within ±1%, in some embodiments within ±0.5% of a number, in some embodiments within ±0.1% of a number unless otherwise stated or otherwise evident from the context (except where such number would impermissibly exceed 100% of a possible value).

Certain claims are presented in dependent form for the sake of convenience, but Applicant reserves the right to rewrite any dependent claim in independent form to include the limitations of the independent claim and any other claim(s) on which such claim depends, and such rewritten claim is to be considered equivalent in all respects to the dependent claim in whatever form it is in (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited.

The invention claimed is:

1. A method of reprogramming a mammalian somatic cell, comprising:
   (I) introducing into the mammalian somatic cell, one or more retroviral vectors encoding Oct4, and optionally encoding one or more reprogramming factors selected from the group consisting of: Klf4 and Sox2, wherein c-Myc is not introduced into the cell;
   (II) contacting the mammalian somatic cell with a Wnt-3a conditioned medium; or an agent that modulates the Wnt pathway selected from the group consisting of a recombinant, exogenous, soluble, and biologically active Wnt protein; and a GSK-3 antagonist; and
   (III) culturing the cells under conditions suitable for reprogramming the mammalian somatic cell to a pluripotent state.

2. The method of claim 1, wherein the method comprises:
   (a) culturing the cell in culture medium containing the agent;
   (b) culturing the cell in culture medium comprising the Wnt-3a conditioned medium or the agent for at least 10 days;
   (c) contacting the cell with the Wnt-3a conditioned medium or the agent that modulates the Wnt pathway, thereby enhancing the number of ES-like cell colonies by at least 5-fold;
   (d) contacting the cell with the Wnt-3a conditioned medium or the agent that modulates the Wnt pathway, thereby enhancing the number of ES-like cell colonies by at least 10-fold;
   (e) culturing the cell in the Wnt3a-conditioned medium;
   (f) contacting the cell with a second agent that modulates the Wnt pathway; or
   (g) culturing the cell in medium containing the recombinant, exogenous, soluble, and biologically active Wnt protein.

3. The method of claim 1, wherein the cell:
   (a) is a human cell;
   (b) is a terminally differentiated cell;
   (c) is a fibroblast; or (d) is modified to express or contain at least one reprogramming factor at levels greater than normally present in cells of that type.

4. The method of claim 2, wherein the recombinant, exogenous, soluble, and biologically active Wnt protein is Wnt3a.

5. The method of claim 1, further comprising:
(a) confirming that the reprogrammed cell is pluripotent;
(b) administering the reprogrammed cell to a subject; or
(c) differentiating the cell to a desired cell type in vitro after reprogramming the cell.

6. The method of claim 1, wherein the method is practiced on:
(a) a population of cells and the method further comprises identifying ES-like cells by morphological criteria;
(b) a population of cells and the method does not comprise imposing chemical selection to select reprogrammed cells; or
(c) a population of cells and the method further comprises separating cells that are reprogrammed to a pluripotent state from cells that are not reprogrammed to a pluripotent state.

7. A composition comprising (i) a mammalian somatic cell that has been modified or treated by introducing one or more polynucleotides encoding Oct4 and optionally encoding one or more reprogramming factors selected from the group consisting of: Klf4, and Sox2, wherein c-Myc is not introduced into the cell; wherein the cell expresses an Oct4 polypeptide and at least one reprogramming factor selected from the group consisting of Klf4 polypeptide, and a Sox2 polypeptide at levels greater than would be the case without such modification or treatment; and (ii) a Wnt-3a conditioned medium; or an agent that increases activity of a Wnt pathway selected from the group consisting of a recombinant, exogenous, soluble, and biologically active Wnt protein; and a GSK-3 antagonist that contributes to reprogramming the somatic cell to a pluripotent state.

8. The composition of claim 7, wherein the somatic cell is not genetically modified to contain another exogenous nucleic acid.

9. A composition comprising:
(a) cell culture medium containing a Wnt-3a conditioned medium; or a Wnt pathway modulator selected from the group consisting of a recombinant, exogenous, soluble, and biologically active Wnt protein; and a GSK-3 antagonist; and
(b) a plurality of mammalian somatic cells, wherein (i) the cells are genetically modified or transiently transfected with one or more polynucleotides encoding Oct4 and optionally encoding one or more reprogramming factors selected from the group consisting of Klf4 and Sox2, wherein c-Myc is not introduced into the cell; (ii) the cells are genetically modified to contain a nucleic acid sequence encoding a selectable marker, operably linked to a promoter for an endogenous pluripotency gene; or (iii) the cell culture medium contains one or more small molecules, nucleic acids, or polypeptides that substitute for a reprogramming factor other than c-Myc.

10. The composition of claim 9, wherein the cell culture medium comprises the Wnt-3a conditioned medium.

11. A composition comprising: an iPS cell and a Wnt-3a conditioned medium; an agent that activates the Wnt pathway selected from the group consisting of a recombinant, exogenous, soluble, and biologically active Wnt protein; and a GSK-3 antagonist.

12. The composition of claim 11, wherein the recombinant, exogenous, soluble, and biologically active Wnt protein is Wnt3a.

\* \* \* \* \*